Figure 2:
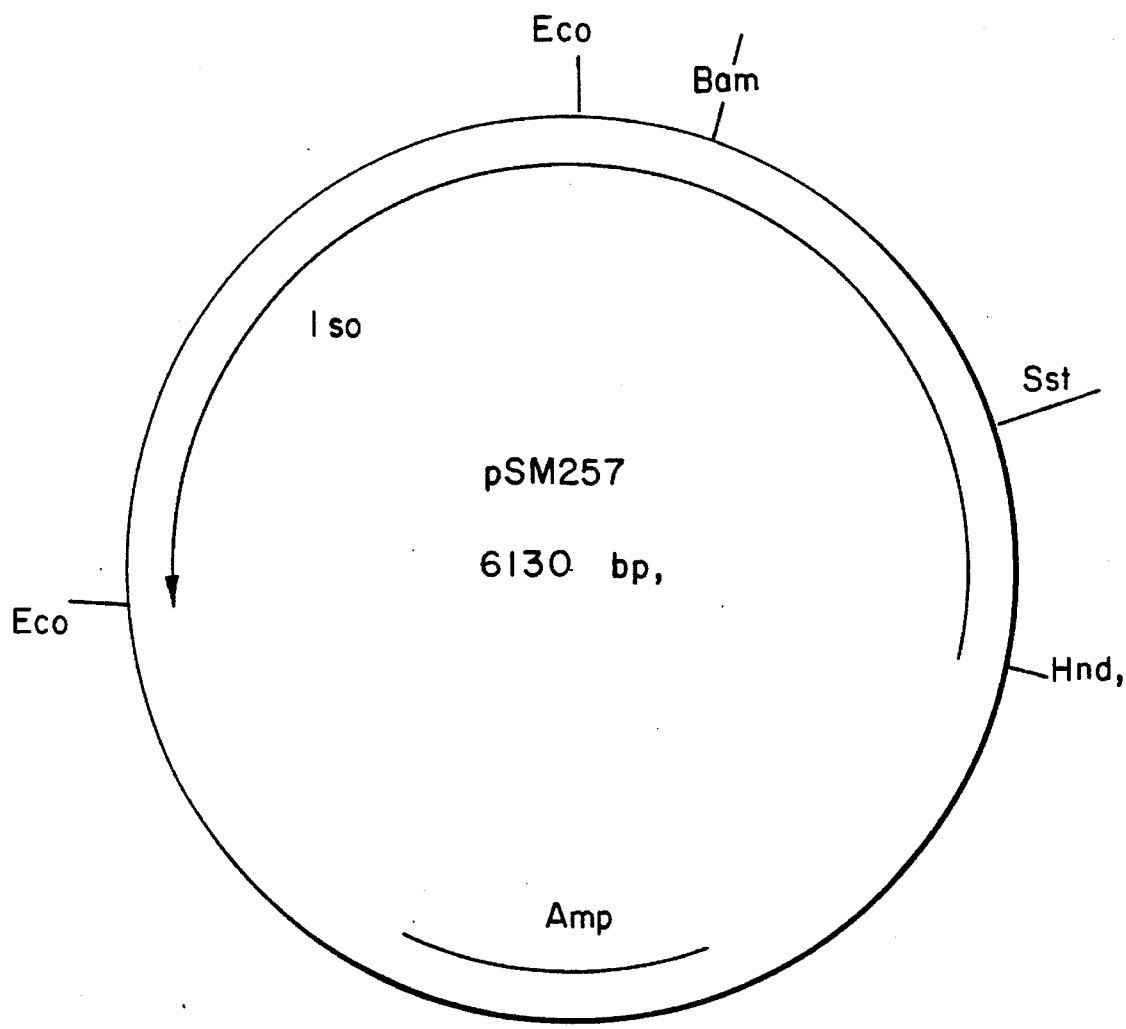

United States Patent [19]

Tognoni et al.

[11] Patent Number: 5,457,037
[45] Date of Patent: Oct. 10, 1995

[54] CLONING OF THE GENE CODING THE ISOAMYLASE ENZYME AND ITS USE IN THE PRODUCTION OF SAID ENZYME

[75] Inventors: Angelo Tognoni; Paolo Carrera, both of Milan; Barbara Camerini, Rome; Giuliano Galli, Rome; Giuseppe Lucchese, Rome; Guido Grandi; Carlo Di Gennaro, both of Milan, all of Italy

[73] Assignee: Enichem Synthesis, S.p.A., Palermo, Italy

[21] Appl. No.: 1,797

[22] Filed: Jan. 8, 1993

Related U.S. Application Data

[63] Continuation of Ser. No. 749,621, Aug. 19, 1991, abandoned, which is a continuation of Ser. No. 224,113, Jul. 25, 1988, abandoned.

[30]     Foreign Application Priority Data

Aug. 7, 1987 [IT] Italy ................................. 21615/87
Jul. 8, 1988 [IT] Italy ................................. 21282/88

[51] Int. Cl.[6] .......................... C12N 1/21; C12N 15/31; C12N 15/75; C12N 9/44
[52] U.S. Cl. ..................... 435/69.8; 435/69.1; 435/210; 435/252.31; 435/252.33; 435/320.1
[58] Field of Search ............................... 435/69.1, 172.3, 435/320.1, 832, 252.31, 839, 69.8

[56]     References Cited

U.S. PATENT DOCUMENTS 4,879,230  11/1989  Takagi et al. .................. 435/172.3

OTHER PUBLICATIONS

H. Urlaub et al (1975) FEBS Letters 57(1): 1–4.
Takahara et al., The Journal of Biological Chemistry, vol. 260, No. 5, (Mar. 10, 1985), pp. 2670–2674.
J. Chen et al., Abstracts of Annual Meeting, ASM, 1986, p. 128, Abstract H–6.
S. V. Suggs et al., Proc. Natl. Acad. Sci., vol. 78, No. 11 (Nov. 1981), pp. 6613–6617.
Martha A. Post–Beittenmiller et al., Molecular & Cellular Biology, vol. 4, (Jul. 1984), pp. 1238–1245 (No. 7).
Ursula Peschke et al., J. Mol. Biol., vol. 186 (1985), pp. 547–555.

*Primary Examiner*—Jacqueline Stone
*Assistant Examiner*—Johnny F. Railey, II
*Attorney, Agent, or Firm*—Rogers & Wells

[57]     ABSTRACT

The structural gene encoding isoamylase from Pseudomonas SMP 1 is obtained. Also described are vectors comprising the isoamylase gene and host microorganisms transformed by these vectors. The transformed host microorganisms are capable of expressing and/or secreting mature isoamylase having biological activity.

3 Claims, 18 Drawing Sheets

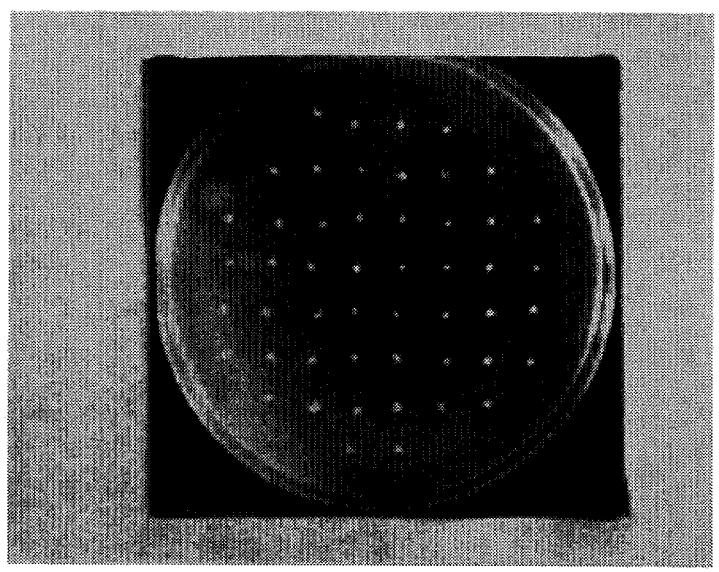
FIG. IA
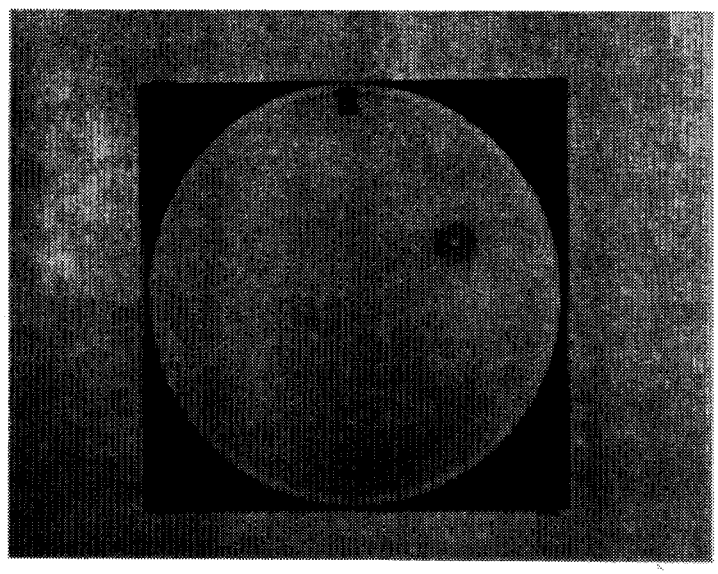
FIG. IB

```
       10         20         30         40         50         60
GATCTGCCGT TCAACACAGT GCAGAACACG CGCTTCCAGT CCATTTCCAG TCCATGGAAG 70         80         90        100        110        120
ACGTGCACCT GTGGATGATC GAGCAGCACT TGGGGCGGCG TACGGTGTCC GATTTCCAGC 130        140        150        160        170        180
GTGGCGTGCT GGCGCTGCGC AACGGCGAGA TCCTGGCGGA CGGTCGCTCG CGGGCAAAGC 190        200        210        220        230        240
CAGCGCAGGA CGAAGCGGTA GCGTGCCAGC AACCGACGAG CGCCGGACGT TGCGGTGCAA 250        260        270        280        290        300
GAGCCTGCGG ACGCACCGCC CGTCGGCAAG GGCAAGGCCG AGCCCCTGCC AAGCCGGCAG 310        320        330        340        350        360
GAGCTTGCGC GCGAAGCTGA GCAACAGCCA GGTGGTGATG ATCGAGAAGA TCCAGAAGCA 370        380        390        400        410        420
GGCCGCGCCC GAAGTGGTCG CGGCGGTCAA GTCTGGCGCG CTGTCGATTC AACGCGGCGG 430        440        450        460        470        480
CAGCCGTGGC GACCCTGCCG GAGGAAGAGC AACGCGCAGC CGCCATCGCT GGCGATGACG 490        500        510        520        530        540
AGCTCAAGCA AGCGGCCAAG CGTGTGCGCG ACGCCAAGCG CAAGCCGAAG AAGGAGCCGG 550        560        570        580        590        600
AGGCGGGCGA GGAGGATCTA CCGACCTTGC GCCGACGCGT GACGGAATTG ACAGCGGAAG 610        620        630        640        650        660
TCGCCGAACT GAAGGCGGAC AACGAAGCGC TGCGTGAAGCA GCTCGCCGGC TGGGAGCGCT 670        680        690        700        710        720
CGGCCAACGC GTGATGCGTG TCTGGACATA GTCCGCAATG AATACGTATG CAATGACTGG 730        740        750        760        770        780
TTGCTGCATT GCGATGCTTT CTACGATGCA TCGCACTGCC GACCAGGTGG CGGCCGCACG 790        800        810        820        830        840
TGGGGAGTGC GTGCGGCACG CCGTGGGATG TCTGATCCGC TTTTCCCGTT TCTCTATTCG 850        860        870        880        890        900
ACAGTGGTTT TCGCTTGCCC GCACGCTGCG GCAAGGATGC GCGCCGTGGC GCCGATGCTG 910        920        930        940        950        960
TTCGACCTGA TCGTCAACGA AACAGGATGG AGGCTGACCC ATGAAGTGCC CAAAGATTCT 970        980        990       1000       1010       1020
CGCCGCGCTG CTTGGCTGCG CGGTGCTCGC TGGTGTGCCC GCAATGCCGG CGCATGCGGC 1030       1040       1050       1060       1070       1080
CATCAACAGC ATGAGCCTGG GCGCGAGCTA CGACGCGCAA CAGGCCAACA TCACCTTTCG 1090       1100       1110       1120       1130       1140
CGTTTACTCC TCGCAGGCCA CGCGCATCGT GCTGTACCTC TATTCGGCAG GTTACGGTGT 1150       1160       1170       1180       1190       1200
GCAGGAGTCG GCCACCTACA CGCTGAGCCC AGCGGGCAGT GGTGTATGGG CGGTGACGGT
```

FIG. 7

```
      1210       1220       1230       1240       1250       1260
GCCGGTGTCG TCGATCAAGG CGGCCGGCAT CACGGGGGCG GTGTACTACG GGTATCGCGC 1270       1280       1290       1300       1310       1320
CTGGGGGCCG AATTGGCCTT ATGCCAGCAA CTGGGGCAAG GGTTCGCAGG CGGGCTTTGT 1330       1340       1350       1360       1370       1380
TTCCGACGTC GACGCCAACG GCGACCGCTT CAATCCCAAC AAACTGTTGT TGGACCCCTA 1390       1400       1410       1420       1430       1440
CGCGCAGGAA GTGAGCCAGG ATCCGCTGAA CCCGTCCAAC CAGAACGGCA ACGTGTTCGC 1450       1460       1470       1480       1490       1500
CTCTGGCGCC AGCTATCGCA CCACCGACAG TGGCATCTAT GCACCCAAGG GTGTCGTGCT 1510       1520       1530       1540       1550       1560
GGTGCCCAGT ACGCAAAGTA CCGGCACCAA ACCCACACGC GCGCAGAAGG ATGATGTGAT 1570       1580       1590       1600       1610       1620
CTACGAGGTG CATGTGCGCG GCTTCACCGA GCAGGACACC TCTATCCCTG CGCAGTATCG 1630       1640       1650       1660       1670       1680
CGGCACCTAT TACGGTGCAG GGCTCAAGGC CAGTTACCTC GCCAGCCTGG GCGTGACCGC 1690       1700       1710       1720       1730       1740
GGTGGAATTC CTGCCGGTGC AGGAAACGCA GAATGATGCG AACGATGTGG TTCCCAATTC 1750       1760       1770       1780       1790       1800
AGATGCCAAC CAGAACTACT GGGGCTACAT GACCGAGAAC TACTTCTCGC CGGATCGCCG 1810       1820       1830       1840       1850       1860
CTATGCCTAC AACAAGGCGG CTGGCGGTCC CACGGCGGAG TTCCAGGCGA TGGTGCAGGC 1870       1880       1890       1900       1910       1920
GTTTCACAAC GCAGGCATCA AGTCTACAT GGATGTGGTC TACAACCACA CCGCCGAAGG 1930       1940       1950       1960       1970       1980
CGGCACCTGG ACCAGCAGTG ATCCCACCAC GGCCACCATT TATTCGTGGC GCGGCTTGGA 1990       2000       2010       2020       2030       2040
CAATACCACG TACTACGAGC TGACCTCGGG CAACCAATAC TTCTACGACA ACACGGGCAT 2050       2060       2070       2080       2090       2100
TGGCGCGAAC TTCAATACGT ACAACACGGT GGCGCAGAAC CTTATCGTCG ACTCGCTGGC 2110       2120       2130       2140       2150       2160
GTATTGGGCG AACACGATGG GCGTGGATGG CTTTCGCTTC GACCTTGCTT CCGTGCTCGG 2170       2180       2190       2200       2210       2220
CAACAGTTGC CTCAATGGCG CGTACACGGC GTCCGCGCCC AATTGCCCGA ACGGTGGTTA 2230       2240       2250       2260       2270       2280
TAACTTCGAC GCGGCGGATA GCAACGTAGC GATCAACCGC ATCCTACGCG AGTTCACGGT 2290       2300       2310       2320       2330       2340
GCGCCCGGCG GCGGGCGGCA GCGGTCTGGA TCTGTTTGCG GAACCTTGGG CCATCGGCGG 2350       2360       2370       2380       2390       2400
CAACTCGTAC CAGCTGGGTG GATTCCCGCA GGGTTGGTCC GAGTGGAATG GTCTGTTCCG
```

FIG. 7A

```
       2410       2420       2430       2440       2450       2460
 CGACAGCCTG CGGCAGGCGC AGAACGAGCT GGGTAGCATG ACCATCTATG TGACGCAGGA 2470       2480       2490       2500       2510       2520
 TGCGAATGAT TTCTCCGGTT CGTCCAATCT GTTCCAGTCC AGTGGGCGGT CGCCGTGGAA 2530       2540       2550       2560       2570       2580
 CTCGATCAAC TTTATCGACG TGCATGACGG CATGACGTTG AAGGACGTGT ACTCCTGCAA 2590       2600       2610       2620       2630       2640
 CGGCGCCAAC AACAGTCAGG CGTGGCCCTA CGGGCCGTCG GATGGCGGCA CGAGCACCAA 2650       2660       2670       2680       2690       2700
 TTACAGTTGG GATCAGGGCA TGTCGGCGGG AACGGGTGCC GCGGTCGACC AGCGTCGAGC 2710       2720       2730       2740       2750       2760
 GGCACGAACG GGCATGGCCT TCGAGATGTT GTCGGCGGGC ACGCCGCTGA TGCAGGGCGG 2770       2780       2790       2800       2810       2820
 CGACGAATAC CTGCGCACGC TCCAGTGCAA CAACAATGCC TACAACCTCG ACTCCAGCGC 2830       2840       2850       2860       2870       2880
 CAACTGGCTT ACCTATAGCT GGACCACCGA TCAATCGAAC TTCTACACCT TCGCGCAACG 2890       2900       2910       2920       2930       2940
 CCTCATTGCG TTCCGCAAGG CACATCCCGC GCTTCGCCCG TCGAGCTGGT ACAGCGGCAG 2950       2960       2970       2980       2990       3000
 CCAGTTGACG TGGTATCAGC CCAGTGGAGC CGTGGCGGAC AGCAACTACT GGAACAACAC 3010       3020       3030       3040       3050       3060
 CAGCAACTAC GCCATTGCCT ACGCCATCAA TGGGCCTTCG CTGGGCGACA GCAATTCCAT 3070       3080       3090       3100       3110       3120
 CTATGTCGCT TACAACGGTT GGTCGAGCAG CGTGACTTTC ACCTTGCCTG CGCCACCGTC 3130       3140       3150       3160       3170       3180
 AGGCACGCAG TGGTATCGCG TCACGGATAC CTGCGACTGG AACGATGGCG CCAGTACGTT 3190       3200       3210       3220       3230       3240
 TGTTGCACCG GGCAGCGAGA CATTGATCGG CGGCGCGGGC ACCACCTATG GCAATGCGG 3250       3260       3270       3280       3290       3300
 TCAATCGCTG CTGCTGTTGA TCTCCAAGTA GCCATGGGGC ACGAGCGTTA CCCAAAACGGG 3310       3320       3330
 TACCGCTGGT GCAATAGGTC TGGCTGACGT GTTTGTC
```

FIG. 7B

```
                                    30                                                       60
GCC ATC AAC AGC ATG AGC CTG GGC GCG AGC TAC GAC GCG CAA CAG GCC AAC ATC ACC TTT
Ala Ile Asn Ser Met Ser Leu Gly Ala Ser Tyr Asp Ala Gln Gln Ala Asn Ile Thr Phe 90                                                      120
CGC GTT TAC TCC TCG CAG GCC ACG CGC ATC GTG CTG TAC CTC TAT TCG GCA GGT TAC GGT
Arg Val Tyr Ser Ser Gln Ala Thr Arg Ile Val Leu Tyr Leu Tyr Ser Ala Gly Tyr Gly 150                                                      180
GTG CAG GAG TCG GCC ACC TAC ACG CTG AGC CCA GCG GGC AGT GGT GTA TGG GCG GTG ACG
Val Gln Glu Ser Ala Thr Tyr Thr Leu Ser Pro Ala Gly Ser Gly Val Trp Ala Val Thr 210                                                      240
GTG CCG GTG TCG TCG ATC AAG GCG GCC GGC ATC ACG GGG GCG GTG TAC TAC GGG TAT CGC
Val Pro Val Ser Ser Ile Lys Ala Ala Gly Ile Thr Gly Ala Val Tyr Tyr Gly Tyr Arg 270                                                      300
GCC TGG GGG CCG AAT TGG CCT TAT GCC AGC AAC TGG GGC AAG GGT TCG CAG GCG GGC TTT
Ala Trp Gly Pro Asn Trp Pro Tyr Ala Ser Asn Trp Gly Lys Gly Ser Gln Ala Gly Phe 330                                                      360
GTT TCC GAC GTC GAC GCC AAC GGC GAC CGC TTC AAT CCC AAC AAA CTG TTG TTG GAC CCC
Val Ser Asp Val Asp Ala Asn Gly Asp Arg Phe Asn Pro Asn Lys Leu Leu Leu Asp Pro 390                                                      420
TAC GCG CAG GAA GTG AGC CAG GAT CCG CTG AAC CCG TCC AAC CAG AAC GGC AAC GTG TTC
Tyr Ala Gln Glu Val Ser Gln Asp Pro Leu Asn Pro Ser Asn Gln Asn Gly Asn Val Phe 450                                                      480
GCC TCT GGC GCC AGC TAT CGC ACC ACC GAC AGT GGC ATC TAT GCA CCC AAG GGT GTC GTG
Ala Ser Gly Ala Ser Tyr Arg Thr Thr Asp Ser Gly Ile Tyr Ala Pro Lys Gly Val Val 510                                                      540
CTG GTG CCC AGT ACG CAA AGT ACC GGC ACC AAA CCC ACA CGC GCG CAG AAG GAT GAT GTG
Leu Val Pro Ser Thr Gln Ser Thr Gly Thr Lys Pro Thr Arg Ala Gln Lys Asp Asp Val 570                                                      600
ATC TAC GAG GTG CAT GTG CGC GGC TTC ACC GAG CAG GAC ACC TCT ATC CCT GCG CAG TAT
Ile Tyr Glu Val His Val Arg Gly Phe Thr Glu Gln Asp Thr Ser Ile Pro Ala Gln Tyr 630                                                      660
CGC GGC ACC TAT TAC GGT GCA GGG CTC AAG GCC AGT TAC CTC GCC AGC CTG GGC GTG ACC
Arg Gly Thr Tyr Tyr Gly Ala Gly Leu Lys Ala Ser Tyr Leu Ala Ser Leu Gly Val Thr 690                                                      720
GCG GTG GAA TTC CTG CCG GTG CAG GAA ACG CAG AAT GAT GCG AAC GAT GTG GTT CCC AAT
Ala Val Glu Phe Leu Pro Val Gln Glu Thr Gln Asn Asp Ala Asn Asp Val Val Pro Asn 750                                                      780
TCA GAT GCC AAC CAG AAC TAC TGG GGC TAC ATG ACC GAG AAC TAC TTC TCG CCG GAT CGC
Ser Asp Ala Asn Gln Asn Tyr Trp Gly Tyr Met Thr Glu Asn Tyr Phe Ser Pro Asp Arg 810                                                      840
CGC TAT GCC TAC AAC AAG GCG GCT GGC GGT CCC ACG GCG GAG TTC CAG GCG ATG GTG CAG
Arg Tyr Ala Tyr Asn Lys Ala Ala Gly Gly Pro Thr Ala Glu Phe Gln Ala Met Val Gln 870                                                      900
GCG TTT CAC AAC GCA GGC ATC AAG GTC TAC ATG GAT ATG GTC TAC AAC CAC ACC GCC GAA
Ala Phe His Asn Ala Gly Ile Lys Val Tyr Met Asp Met Val Tyr Asn His Thr Ala Glu
```

FIG. 8

```
                                         930                                              960
GGC GGC ACC TGG ACC AGC AGT GAT CCC ACC ACG GCC ACC ATT TAT TCG TGG CGC GGC TTG
Gly Gly Thr Trp Thr Ser Ser Asp Pro Thr Thr Ala Thr Ile Tyr Ser Trp Arg Gly Leu
                                         990                                             1020
GAC AAT ACC ACG TAC TAC GAG CTG ACC TCG GGC AAC CAA TAC TTC TAC GAC AAC ACG GGC
Asp Asn Thr Thr Tyr Tyr Glu Leu Thr Ser Gly Asn Gln Tyr Phe Tyr Asp Asn Thr Gly
                                        1050                                             1080
ATT GGC GCG AAC TTC AAT ACG TAC AAC ACG GTG GCG CAG AAC CTT ATC GTC GAC TCG CTG
Ile Gly Ala Asn Phe Asn Thr Tyr Asn Thr Val Ala Gln Asn Leu Ile Val Asp Ser Leu
                                        1110                                             1140
GCG TAT TGG GCG AAC ACG ATG GGC GTG GAT GGC TTT CGC TTC GAC CTT GCT TCC GTG CTC
Ala Tyr Trp Ala Asn Thr Met Gly Val Asp Gly Phe Arg Phe Asp Leu Ala Ser Val Leu
                                        1170                                             1200
GGC AAC AGT TGC CTC AAT GGC GCG TAC ACG GCG TCC GCG CCC AAT TGC CCG AAC GGT GGT
Gly Asn Ser Cys Leu Asn Gly Ala Tyr Thr Ala Ser Ala Pro Asn Cys Pro Asn Gly Gly
                                        1230                                             1260
TAT AAC TTC GAC GCG GCG GAT AGC AAC GTA GCG ATC AAC CGC ATC CTA CGC GAG TTC ACG
Tyr Asn Phe Asp Ala Ala Asp Ser Asn Val Ala Ile Asn Arg Ile Leu Arg Glu Phe Thr
                                        1290                                             1320
GTG CGC CCG GCG GCG GGC GGC AGC GGT CTG GAT CTG TTT GCG GAA CCT TGG GCC ATC GGC
Val Arg Pro Ala Ala Gly Gly Ser Gly Leu Asp Leu Phe Ala Glu Pro Trp Ala Ile Gly
                                        1350                                             1380
GGC AAC TCG TAC CAG CTG GGT GGA TTC CCG CAG GGT TGG TCC GAG TGG AAT GGT CTG TTC
Gly Asn Ser Tyr Gln Leu Gly Gly Phe Pro Gln Gly Trp Ser Glu Trp Asn Gly Leu Phe
                                        1410                                             1440
CGC GAC AGC CTG CGG CAG GCG CAG AAC GAG CTG GGT AGC ATG ACC ATC TAT GTC ACG CAG
Arg Asp Ser Leu Arg Gln Ala Gln Asn Glu Leu Gly Ser Met Thr Ile Tyr Val Thr Gln
                                        1470                                             1500
GAT GCG AAT GAT TTC TCC GGT TCG TCC AAT CTG TTC CAG TCC AGT GGG CGG TCG CCG TGG
Asp Ala Asn Asp Phe Ser Gly Ser Ser Asn Leu Phe Gln Ser Ser Gly Arg Ser Pro Trp
                                        1530                                             1560
AAC TCG ATC AAC TTT ATC GAC GTG CAT GAC GGC ATG ACG TTG AAG GAC GTG TAC TCC TGC
Asn Ser Ile Asn Phe Ile Asp Val His Asp Gly Met Thr Leu Lys Asp Val Tyr Ser Cys
                                        1590                                             1620
AAC GGC GCC AAC AAC AGT CAG GCG TGG CCC TAC GGG CCG TCG GAT GGC GGC ACG AGC ACC
Asn Gly Ala Asn Asn Ser Gln Ala Trp Pro Tyr Gly Pro Ser Asp Gly Gly Thr Ser Thr
                                        1650                                             1680
AAT TAC AGT TGG GAT CAG GGC ATG TCG GCG GGA ACG GGT GCC GCG GTC GAC CAG CGT CGA
Asn Tyr Ser Trp Asp Gln Gly Met Ser Ala Gly Thr Gly Ala Ala Val Asp Gln Arg Arg
                                        1710                                             1740
GCG GCA CGA ACG GGC ATG GCC TTC GAG ATG TTG TCG GCG GGC ACG CCG CTG ATG CAG GGC
Ala Ala Arg Thr Gly Met Ala Phe Glu Met Leu Ser Ala Gly Thr Pro Leu Met Gln Gly
                                        1770                                             1800
GGC GAC GAA TAC CTG CGC ACG CTC CAG TGC AAC AAC AAT GCC TAC AAC CTC GAC TCC AGC
```

FIG. 8A

```
                Gly Asp Glu Tyr Leu Arg Thr Leu Gln Cys Asn Asn Asn Ala Tyr Asn Leu Asp Ser Ser
                                    1830                                              1860
GCC AAC TGG CTT ACC TAT AGC TGG ACC ACC GAT CAA TCG AAC TTC TAC ACC TTC GCG CAA
Ala Asn Trp Leu Thr Tyr Ser Trp Thr Thr Asp Gln Ser Asn Phe Tyr Thr Phe Ala Gln
                                    1890                                              1920
CGC CTC ATT GCG TTC CGC AAG GCA CAT CCC GCG CTT CGC CCG TCG AGC TGG TAC AGC GGC
Arg Leu Ile Ala Phe Arg Lys Ala His Pro Ala Leu Arg Pro Ser Ser Trp Tyr Ser Gly
                                    1950                                              1980
AGC CAG TTG ACG TGG TAT CAG CCC AGT GGA GCC GTG GCG GAC AGC AAC TAC TGG AAC AAC
Ser Gln Leu Thr Trp Tyr Gln Pro Ser Gly Ala Val Ala Asp Ser Asn Tyr Trp Asn Asn
                                    2010                                              2040
ACC AGC AAC TAC GCC ATT GCC TAC GCC ATC AAT GGG CCT TCG CTG GGC GAC AGC AAT TCC
Thr Ser Asn Tyr Ala Ile Ala Tyr Ala Ile Asn Gly Pro Ser Leu Gly Asp Ser Asn Ser
                                    2070                                              2100
ATC TAT GTC GCT TAC AAC GGT TGG TCG AGC AGC GTG ACT TTC ACC TTG CCT GCG CCA CCG
Ile Tyr Val Ala Tyr Asn Gly Trp Ser Ser Ser Val Thr Phe Thr Leu Pro Ala Pro Pro
                                    2130                                              2160
TCA GGC ACG CAG TGG TAT CGC GTC ACG GAT ACC TGC GAC TGG AAC GAT GGC GCC AGT ACG
Ser Gly Thr Gln Trp Tyr Arg Val Thr Asp Thr Cys Asp Trp Asn Asp Gly Ala Ser Thr
                                    2190                                              2220
TTT GTT GCA CCG GGC AGC GAG ACA TTG ATC GGC GGC GCG GGC ACC ACC TAT GGG CAA TGC
Phe Val Ala Pro Gly Ser Glu Thr Leu Ile Gly Gly Ala Gly Thr Thr Tyr Gly Gln Cys
                                    2250
GGT CAA TCG CTG CTG CTG TTG ATC TCC AAG TAG
Gly Gln Ser Leu Leu Leu Leu Ile Ser Lys End
```

FIG. 8B

```
          10        20        30        40        50        60
ATGACTGGTTGCTGCATTGCGATGCTTTCTACGATGCATCGCACTGCCGACCAGGTGGCG 70        80        90       100       110       120
GCCGCACGTGGGGAGTGCGTGCGGCACGCCGTGGGATGTCTGATCCGCTTTTCCCGTTTC 130       140       150       160       170       180
TCTATTCGACAGTGGTTTTCGCTTGCCCGCACGCTGCGGCAAGGATGCGCGCCGTGGCGC 190       200       210       220       230       240
CGATGCTGTTCGACCTGATCGTCAACGAAACAGGATGGAGGCTGACCCATGAAGTGCCCA
                                      RBS         MetLysCysPro
                                                  LS
         250       260       270       280       290       300
AAGATTCTCGCCGCGCTGCTTGGCTGCGCGGTGCTCGCTGGTGTGCCCGCAATGCCGGCG
LysIleLeuAlaAlaLeuLeuGlyCysAlaValLeuAlaGlyValProAlaMetProAla 310       320       330       340       350       360
CATGCGGCCATCAACAGCATGAGCCTGGGCGCGAGCTACGACGCGCAACAGGCCAACATC
HisAlaAlaIleAsnSerMetSerLeuGlyAlaSerTyrAspAlaGlnGlnAlaAsnIle 370       380       390       400       410       420
ACCTTTCGCGTTTACTCCTCGCAGGCCACGCGCATCGTGCTGTACCTCTATTCGGCAGGT
ThrPheArgValTyrSerSerGlnAlaThrArgIleValLeuTyrLeuTyrSerAlaGly 430       440       450       460       470       480
TACGGTGTGCAGGAGTCGGCCACCTACACGCTGAGCCCAGCGGGCAGTGGTGTATGGGCE
TyrGlyValGlnGluSerAlaThrTyrThrLeuSerProAlaGlySerGlyValTrpAla 490       500       510       520       530       540
GTGACGGTGCCGGTGTCGTCGATCAAGGCGGCCGGCATCACGGGGGCGGTGTACTACGGG
ValThrValProValSerSerIleLysAlaAlaGlyIleThrGlyAlaValTyrTyrGly 550       560       570       580       590       600
TATCGCGCCTGGGGGCCGAATTGGCCTTATGCCAGCAACTGGGGCAAGGGTTCGCAGGCG
TyrArgAlaTrpGlyProAsnTrpProTyrAlaSerAsnTrpGlyLysGlySerGlnAla 610       620       630       640       650       660
GGCTTTGTTTCCGACGTCGACGCCAACGGCGACCGCTTCAATCCCAACAAACTGTTGTTG
GlyPheValSerAspValAspAlaAsnGlyAspArgPheAsnProAsnLysLeuLeuLeu 670       680       690       700       710       720
GACCCCTACGCGCAGGAAGTGAGCCAGGATCCGCTGAACCCGTCCAACCAGAACGGCAAC
AspProTyrAlaGlnGluValSerGlnAspProLeuAsnProSerAsnGlnAsnGlyAsn 730       740       750       760       770       780
GTGTTCGCCTCTGGCGCCAGCTATCGCACCACCGACAGTGGCATCTATGCACCCAAGGGT
ValPheAlaSerGlyAlaSerTyrArgThrThrAspSerGlyIleTyrAlaProLysGly 790       800       810       820       830       840
GTCGTGCTGGTGCCCAGTACGCAAAGTACCGGCACCAAACCCACACGCGCGCAGAAGGAT
ValValLeuValProSerThrGlnSerThrGlyThrLysProThrArgAlaGlnLysAsp 850       860       870       880       890       900
GATGTGATCTACGAGGTGCATGTGCGCGGCTTCACCGAGCAGGACACCTCTATCCCTGCG
AspValIleTyrGluValHisValArgGlyPheThrGluGlnAspThrSerIleProAla
```

FIG. 9

```
         910       920       930       940       950       960
CAGTATCGCGGCACCTATTACGGTGCAGGGCTCAAGGCCAGTTACCTCGCCAGCCTGGGC
GlnTyrArgGlyThrTyrTyrGlyAlaGlyLeuLysAlaSerTyrLeuAlaSerLeuGly 970       980       990      1000      1010      1020
GTGACCGCCGTGGAATTCCTGCCGGTGCAGGAAACGCAGAATGATGCGAACGATGTGGTT
ValThrAlaValGluPheLeuProValGlnGluThrGlnAsnAspAlaAsnAspValVal 1030      1040      1050      1060      1070      1080
CCCAATTCAGATGCCAACCAGAACTACTGGGGCTACATGACCGAGAACTACTTCTCGCCG
ProAsnSerAspAlaAsnGlnAsnTyrTrpGlyTyrMetThrGluAsnTyrPheSerPro 1090      1100      1110      1120      1130      1140
GATCGCCGCTATGCCTACAACAAGGCGGCTGGCGGTCCCACGGCGGAGTTCCAGGCGATG
AspArgArgTyrAlaTyrAsnLysAlaAlaGlyGlyProThrAlaGluPheGlnAlaMet 1150      1160      1170      1180      1190      1200
GTGCAGGCGTTTCACAACGCAGGCATCAAGGTCTACATGGATGTGGTCTACAACCACACC
ValGlnAlaPheHisAsnAlaGlyIleLysValTyrMetAspValValTyrAsnHisThr 1210      1220      1230      1240      1250      1260
GCCGAAGGCGGCACCTGGACCAGCAGTGATCCCACCACGGCCACCATTTATTCGTGGCGC
AlaGluGlyGlyThrTrpThrSerSerAspProThrThrAlaThrIleTyrSerTrpArg 1270      1280      1290      1300      1310      1320
GGCTTGGACAATACCACCTACTACGAGCTGACCTCGGGCAACCAATACTTCTACGACAAC
GlyLeuAspAsnThrThrTyrTyrGluLeuThrSerGlyAsnGlnTyrPheTyrAspAsn 1330      1340      1350      1360      1370      1380
ACGGGCATTGGCGCGAACTTCAATACGTACAACACGGTGGCGCAGAACCTTATCGTCGAC
ThrGlyIleGlyAlaAsnPheAsnThrTyrAsnThrValAlaGlnAsnLeuIleValAsp 1390      1400      1410      1420      1430      1440
TCGCTGGCGTATTGGGCGAACACGATGGGCGTGGATGGCTTTCGCTTCGACCTTGCTTCC
SerLeuAlaTyrTrpAlaAsnThrMetGlyValAspGlyPheArgPheAspLeuAlaSer 1450      1460      1470      1480      1490      1500
GTGCTCGGCAACAGTTGCCTCAATGGCGCGTACACGGCGTCCGCGCCCAATTGCCCGAAC
ValLeuGlyAsnSerCysLeuAsnGlyAlaTyrThrAlaSerAlaProAsnCysProAsn 1510      1520      1530      1540      1550      1560
GGTGGTTATAACTTCGACGCGGCGGATAGCAACGTAGCGATCAACCGCATCCTACGCGAG
GlyGlyTyrAsnPheAspAlaAlaAspSerAsnValAlaIleAsnArgIleLeuArgGlu 1570      1580      1590      1600      1610      1620
TTCACGGTGCGCCCGGCGGCGGGCGGCAGCGGTCTGGATCTGTTTGCGGAACCTTGGGCC
PheThrValArgProAlaAlaGlyGlySerGlyLeuAspLeuPheAlaGluProTrpAla 1630      1640      1650      1660      1670      1680
ATCGGCGGCAACTCGTACCAGCTGGGTGGATTCCCGCAGGGTTGGTCCGAGTGGAATGGT
IleGlyGlyAsnSerTyrGlnLeuGlyGlyPheProGlnGlyTrpSerGluTrpAsnGly 1690      1700      1710      1720      1730      1740
CTGTTCCGCGACAGCCTGCGGCAGGCGCAGAACGAGCTGGGTAGCATGACCATCTATGTG
LeuPheArgAspSerLeuArgGlnAlaGlnAsnGluLeuGlySerMetThrIleTyrVal 1750      1760      1770      1780      1790      1800
```

FIG. 9A

```
ACGCAGGATGCGAATGATTTCTCCGGTTCGTCCAATCTGTTCCAGTCCAGTGGGCGGTCG
ThrGlnAspAlaAsnAspPheSerGlySerSerAsnLeuPheGlnSerSerGlyArgSer 1810      1820      1830      1840      1850      1860
CCGTGGAACTCGATCAACTTTATCGACGTGCATGACGGCATGACGTTGAAGGACGTGTAC
ProTrpAsnSerIleAsnPheIleAspValHisAspGlyMetThrLeuLysAspValTyr 1870      1880      1890      1900      1910      1920
TCCTGCAACGGCGCCAACAACAGTCAGGCGTGGCCCTACGGGCCGTCGGATGGCGGCACG
SerCysAsnGlyAlaAsnAsnSerGlnAlaTrpProTyrGlyProSerAspGlyGlyThr 1930      1940      1950      1960      1970      1980
AGCACCAATTACAGTTGGGATCAGGGCATGTCGGCGGGAACGGGTGCCGCGGTCGACCAG
SerThrAsnTyrSerTrpAspGlnGlyMetSerAlaGlyThrGlyAlaAlaValAspGln 1990      2000      2010      2020      2030      2040
CGTCGAGCGGCACGAACGGGCATGGCCTTCGAGATGTTGTCGGCGGGCACGCCGCTGATG
ArgArgAlaAlaArgThrGlyMetAlaPheGluMetLeuSerAlaGlyThrProLeuMet 2050      2060      2070      2080      2090      2100
CAGGGCGGCGACGAATACCTGCGCACGCTCCAGTGCAACAACAATGCCTACAACCTCGAC
GlnGlyGlyAspGluTyrLeuArgThrLeuGlnCysAsnAsnAsnAlaTyrAsnLeuAsp 2110      2120      2130      2140      2150      2160
TCCAGCGCCAACTGGCTTACCTATAGCTGGACCACCGATCAATCGAACTTCTACACCTTC
SerSerAlaAsnTrpLeuThrTyrSerTrpThrThrAspGlnSerAsnPheTyrThrPhe 2170      2180      2190      2200      2210      2220
GCGCAACGCCTCATTGCGTTCCGCAAGGCACATCCCGCGCTTCGCCCGTCGAGCTGGTAC
AlaGlnArgLeuIleAlaPheArgLysAlaHisProAlaLeuArgProSerSerTrpTyr 2230      2240      2250      2260      2270      2280
AGCGGCAGCCAGTTGACGTGGTATCAGCCCAGTGGAGCCGTGGCGGACAGCAACTACTGG
SerGlySerGlnLeuThrTrpTyrGlnProSerGlyAlaValAlaAspSerAsnTyrTrp 2290      2300      2310      2320      2330      2340
AACAACACCAGCAACTACGCCATTGCCTACGCCATCAATGGGCCTTCGCTGGGCGACAGC
AsnAsnThrSerAsnTyrAlaIleAlaTyrAlaIleAsnGlyProSerLeuGlyAspSer 2350      2360      2370      2380      2390      2400
AATTCCATCTATGTCGCTTACAACGGTTGGTCGAGCAGCGTGACTTTCACCTTGCCTGCG
AsnSerIleTyrValAlaTyrAsnGlyTrpSerSerSerValThrPheThrLeuProAla 2410      2420      2430      2440      2450      2460
CCACCGTCAGGCACGCAGTGGTATCGCGTCACGGATACCTGCGACTGGAACGATGGCGCC
ProProSerGlyThrGlnTrpTyrArgValThrAspThrCysAspTrpAsnAspGlyAla 2470      2480      2490      2500      2510      2520
AGTACGTTTGTTGCACCGGGCAGCGAGACATTGATCGGCGGCGCGGGCACCACCTATGGG
SerThrPheValAlaProGlySerGluThrLeuIleGlyGlyAlaGlyThrThrTyrGly 2530      2540      2550      2560      2570      2580
CAATGCGGTCAATCGCTGCTGCTGTTGATCTCCAAGTAGCCATGGGCACGAGCGTTACC
GlnCysGlyGlnSerLeuLeuLeuLeuIleSerLysEnd 2590      2600      2610      2620
CAAACGGGTACCGCTGGTGCAATAGGTCTGGCTGACGTGTTTGTC
```

FIG. 9B

CLONING OF THE GENE CODING THE ISOAMYLASE ENZYME AND ITS USE IN THE PRODUCTION OF SAID ENZYME

This is a continuation of application Ser. No. 07/749,621, filed Aug. 19, 1991, now abandoned, which is a continuation of application Ser. No. 07/244,113, filed Jul. 25, 1988, now abandoned.

Invention relates to the technology of recombinant DNA, means and methods using this technology for isolating the DNA sequence and the amino acid sequence derived from isoamylase, the production thereof, the resulting product and its use.

More particularly the invention relates to isolating and sequencing the coding gene for the isoamylase enzyme and specifying the aforementioned enzyme in terms of amino-acid sequence.

Finally the invention relates to molecules of replicable recombinant DNA comprising the isoamylase gene or fragments thereof and host micro-organisms transformed by the aforementioned recombinant DNA molecules and capable of expressing and/or secreting the gene product.

The invention also relates to a method of producing mature isoamylase or peptide fragments thereof capable of expressing a biological activity equivalant to that of mature isoamylase and comprising: cultivation in a suitable culture medium of a micro-organism transformed by a molecule of recombinant DNA containing the isoamylase gene or fragments thereof and separation of the resulting gene product from the culture medium or cells.

The amide comprising a mixture of D(+) glucose polymers in straight-chain form (amylose) or branched (amylopectin) is enzymatically hydrolyzed to produce syrups or solids containing dextrose, maltose and other oligosaccharides. The main enzymes used in hydrolysis of the amide are amylases, which break the type 1-4 glucose bonds present in amylose, and isoamylases and pullulanases, which attack the 1-6 glucoside bond of amylopectin.

Since most amides used industrially for producing maltose contain large quantities of amylopectin, it is necessary to use the two classes of enzymes in combination to obtain maltose with high yields (>95%), In general, enzymes which hydrolyze the 1-6 glucoside bond are produced from a wide range of organisms, varying from unicellular eucaryotes such as yeast (Marno B. and Kobayashi T. (1951) Nature, 167, 606; Gunja Z. H. et al. (1961), Biochem. J., 81, 392) to higher plants (Hobson P. N. et al. (1951), J. Chem. Soc. 1451) and bacteria (Lee E. Y. C. et al. (1968) Arch. Biochem. Biophys., 125, 1028).

More particularly isoamylase (E.C.3.2.1.68), an enzyme having a molecular weight of about 90000 daltons, is produced by fermentation from a strain of *Pseudomonas amyloderamosa* (Harada T. et al. (1968) Appl. Microbiol. 16, 1439).

Owing however to the non-GRAS (Generally Recognized As Safe) character of all species of Pseudomonas, this method is not completely satisfactory.

There is therefore need for a technique for obtaining an isoamylase-producing strain which meets the safety requirements essential for use thereof in the food industry. A micro-organism having the aforementioned characteristics can be obtained by transforming a GRAS organism by recombinant DNA techniques.

Owing to the development of molecular genetics it has become possible, by means of the aforementioned techniques, to combine portions of genetic material of varying origin in vitro, so as to form new combinations of genes, resulting in new hereditary characteristics in certain organisms. In general, the recombinant DNA techniques comprise the following:

Isolating the coding DNA fragment for a given protein;

Inserting the fragment into a cloning vector and isolating the resulting hybrid vector or molecule of recombinant DNA;

Inserting the molecule into a host organism by the transformation technique;

Cultivating the transformed organism so as to express the fragment of DNA consisting in production of the desired protein and finally Isolating and purifying the resulting expressed product from the culture medium or the host organism.

Although this technology has reached high levels of sophistication and numerous studies have been made in this particular sector of the art, it is still difficult to predict success without an effective experimental base. In order to produce heterologous proteins by recombinant DNA techniques, it is essential to have the coding DNA or gene sequence for the protein in question.

Hitherto, neither the sequence of the coding gene for the isoamylase enzyme nor the amino acid sequence of the aforementioned enzyme have been known.

The invention, for the first time, discloses isolation of the gene from isoamylase, sequencing and specification thereof, and the amino acid sequence of the isoamylase enzyme derived from the nucleotide sequence.

The invention also provides information about the sequences above and below the 5' and 3' terminals of the isoamylase gene for bonding it in vitro in a cloning vector for expression.

More particularly, the invention discloses the coding DNA terminal 5' sequence for the secretion-signal peptide (leader sequence) which immediately precedes the amino acid sequence of mature isoamylase and is responsible for secretion thereof.

As a result of all these discoveries, it has become possible to develop means and methods for producing isoamylase via recombinant DNA. Accordingly one object of the invention is a fragment of DNA isolated in pure form and sequenced and comprising the isoamylase gene.

Another object of the invention is specification in terms of amino acid sequence of the mature isoamylase enzyme and of the secretion signal sequence thereof.

Another object of the invention is a molecule of replicable recombinant DNA for expression in a host micro-organism and comprising the DNA fragment or regions thereof.

Another object of the invention is host micro-organisms transformed by the molecule of recombinant DNA and capable of expressing and/or secreting the coded gene product from the heterologous nucleotide sequence contained in the molecule of recombinant DNA.

Another object of the invention is a method of producing mature isoamylase or polypeptides having a biological activity equivalent to that of mature isoamylase and comprising cultivation in a suitable culture medium of a host micro-organism transformed by a molecule of recombinant DNA containing the coding gene for isoamylase or regions thereof, the micro-organism being capable of expressing and/or secreting mature isoamylase or a polyparticle having a biological activity equivalent to that of isoamylase and, finally, separation and purification of the resulting expressed product from the culture medium or the microbial cells.

Another object of the invention is the resulting mature isoamylase enzyme and polypeptides having a biological activity equivalant to that of mature isoamylase.

Another object of the invention is use of the isoamylase enzyme and polypeptides having biological activity equivalent to that of isoamylase in methods of hydrolysis of the 1-6 glucocide bond. Other aims of the invention will be clear from the following text and examples.

In order to understand the invention more clearly, a brief description of the terms used will now be given.

Genome bank— This is the term for all the clones of a host micro-organism, each of which bears a fragment of DNA derived from the donor organism from which the bank is to be obtained.

A genome bank is defined as representative when the set of individual fragments in each clone reconstitutes most (or all) the chromosomal DNA of the organism.

Restriction enzymes are hydrolytic enzymes capable of cutting of DNA molecule at specific sites, which are called the recognition sites of the restriction enzymes.

Cloning vectors are DNA molecules which contain all the genetic information for replication thereof when transferred to a host micro-organism.

Plasmids and the DNA of some bacteriophages are examples of cloning vectors.

Preferably in the technology of recombinant DNA, use is made of the plasmid comprising a DNA double helix in circular form, since a number of copies thereof per cell are present in most bacteria and other micro-organisms. Also, plasmid DNA contains not only the origin of replication for reproducing Itself in the host organism, but also the genes which code selective phenotypic characteristics such as resistance to antibiotics. The advantageous result is easy recognition of the host cells containing the desired plasmid when cultivated on selective media. Plasmids are also useful because they can be cut in specific manner by any of the restriction enzymes, which each recognize a different restriction site in the plasmid DNA.

The heterologous gene or a fragment thereof can subsequently be inserted into the plasmid DNA after cutting, and the ring can be reclosed to form a larger molecule, the molecule of recombinant DNA or hybrid plasmid.

The recombinant DNA molecules are then introduced into host cells by a process called transformation.

The resulting transformed (transforming) cells are then used in a fermentation process for producing the coded polypeptide from the gene inserted into the plasmid by a process called expression.

Expression is the name for the mechanism whereby a host organism is capable of synthesizing the coded protein from a given gene.

It comprises a process of transcription, i.e. transfer of genetic information from DNA to messenger RNA (mRNA) and translation, i.e. transfer of information from mRNA to the protein in accordance with the rules of the genetic code described by J. D. Watson (Molecular Biology of the Gene, W. A. Benjamin Inc. N.Y. 3rd ed. 1976), which refers to the codons, i.e. the triplets of coding nucleotide bases for a given amino acid.

Various codons can code for the same amino acid, but for each amino acid there are only those particular codons and no others. Transcription begins in a region known as the promotor, which is recognized and bonded by the polymerase RNA.

The resulting mRNA is then translated into a polypeptide having the coded amino acid sequence from the messenger RNA.

The translation begins in accordance with the beginning signal (ATG) and ends at the termination codons.

A primer is an oligonucleotide, usually containing 15 to 20 bases, and complementary to that region of the single helix which is to be sequenced by the enzyme method.

A gene is a nucleotide sequence comprising the structural gene, i.e. the sequence of coding bases for the mature protein, above which are the transcription regulating sequences (the promotor and the site where transcription begins), the ribosome attachment site and, in the case of secreted proteins, the coding nucleotide sequence for the secretion-signal peptide of the mature protein, i.e. a protein without amino acid sequences extraneous to the natural protein.

BRIEF DESCRIPTION OF THE DIAGRAMS

FIG. 1: Plates of M9+amylopectin agar medium (pH 6.0) containing some clones from the Sau3A genome bank. After dyeing with iodine, clones 9(A) and 17(B) show the violet ring indicating isoamylase activity.

FIG. 2: Restriction map of plasmid pSM257 extracted from clone 9.

Figure 3:
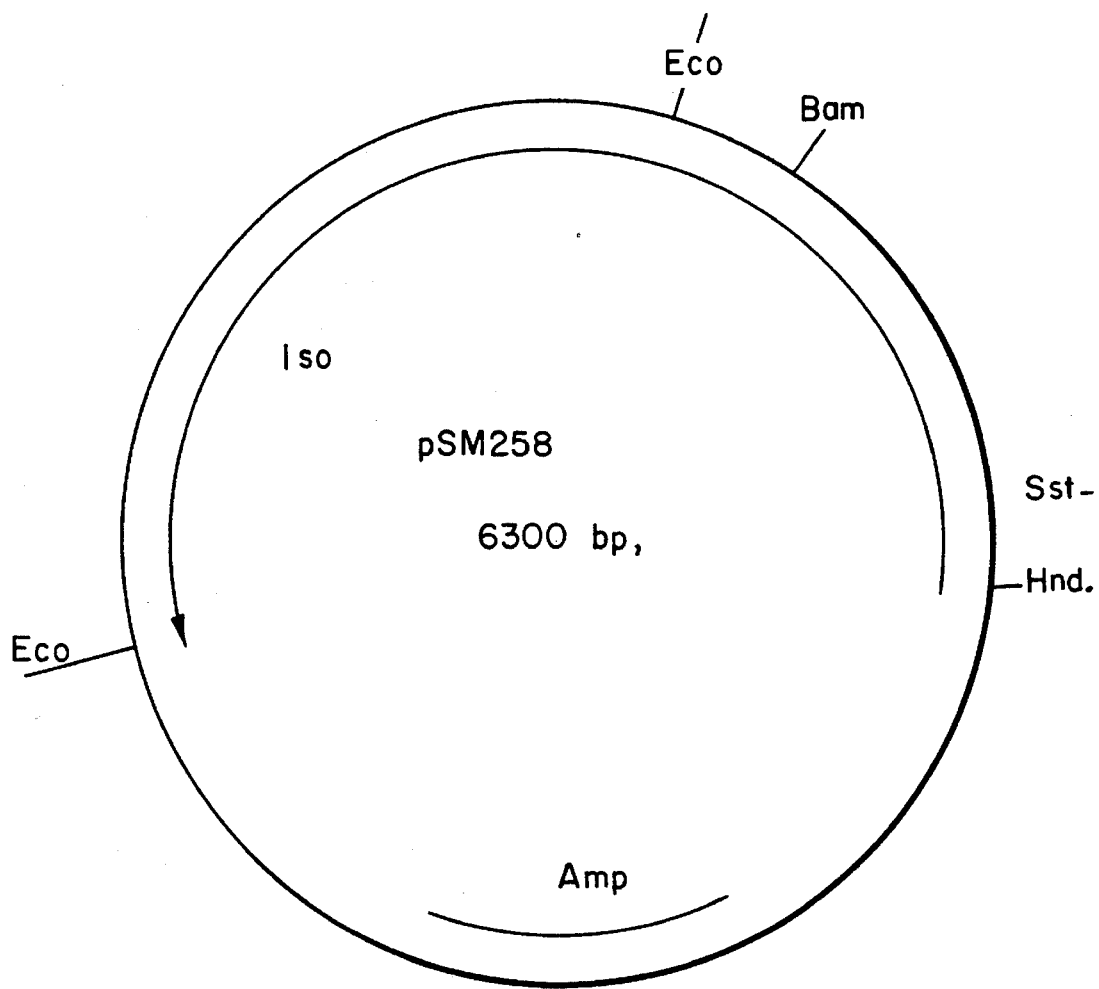

FIG. 3: Restriction map of plasmid pSM258 extracted from clone 17.

Figure 4:
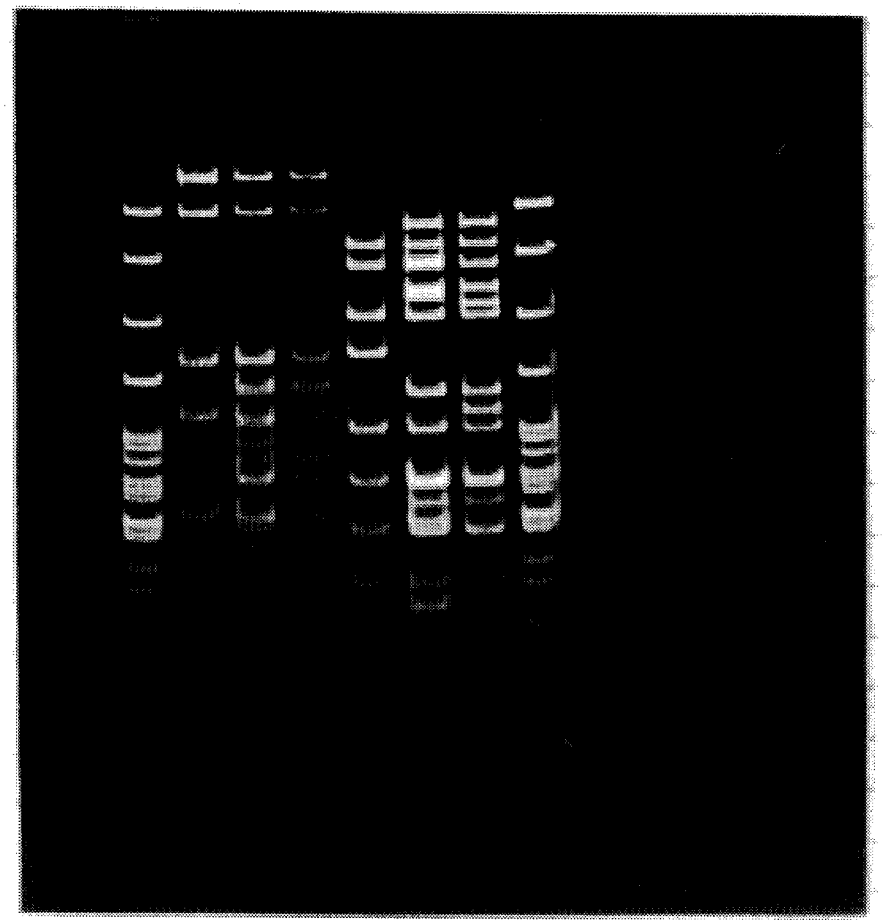

FIG. 4: Comparative analysis of the electrophoretic profiles of hybrid plasmids after digestion with restriction enzymes. The plasmid of clone 9 (pSM257) was digested by Sau3A (2) and HpaII (5) enzymes and compared with the plasmid from clone 17 (pSM 256) (3 and 6) and with the single vector pUC12 (1 and 4).

M: Marker of molecular weights

Figure 5:
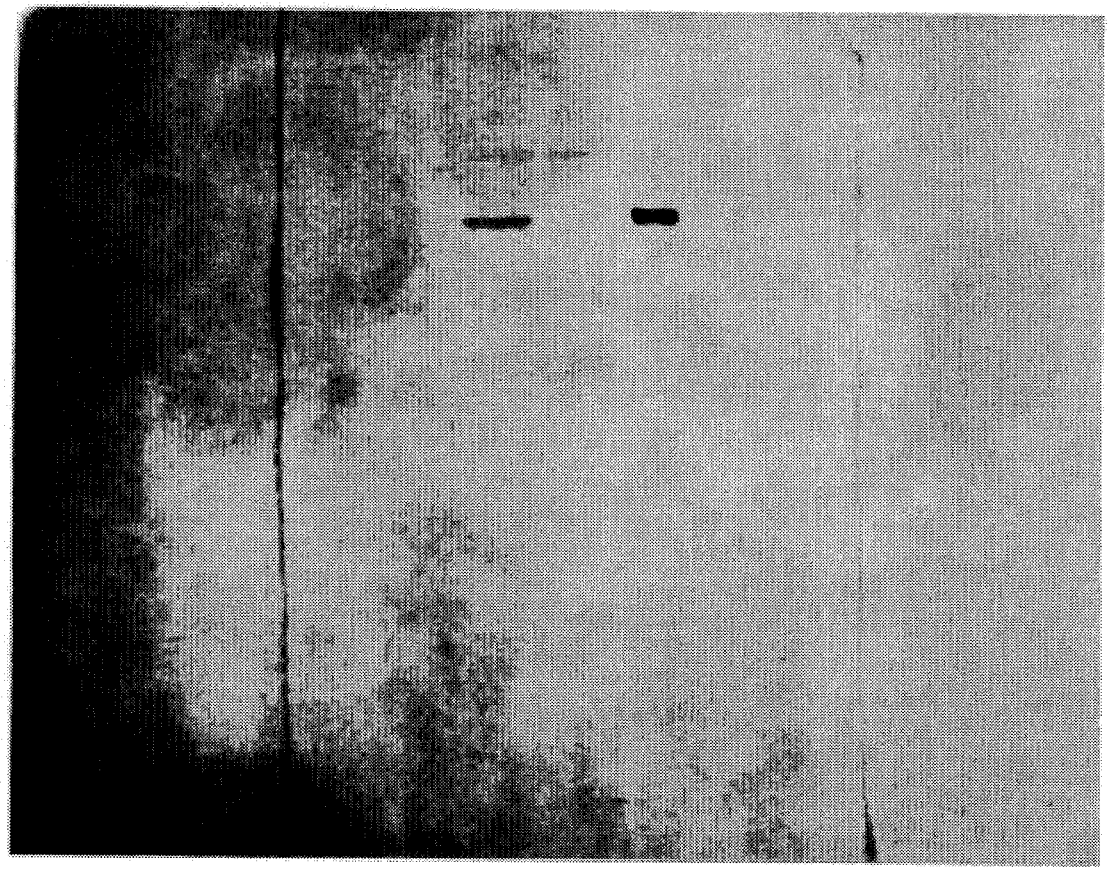

FIG. 5: Analysis of the presence of isoamylase by treatment with anti-isoamylase antibodies.
1. Proteins from clone 9;
2. Proteins from E. coli 71/18;
3. 100 ng of purified isoamylase.

Figure 6:
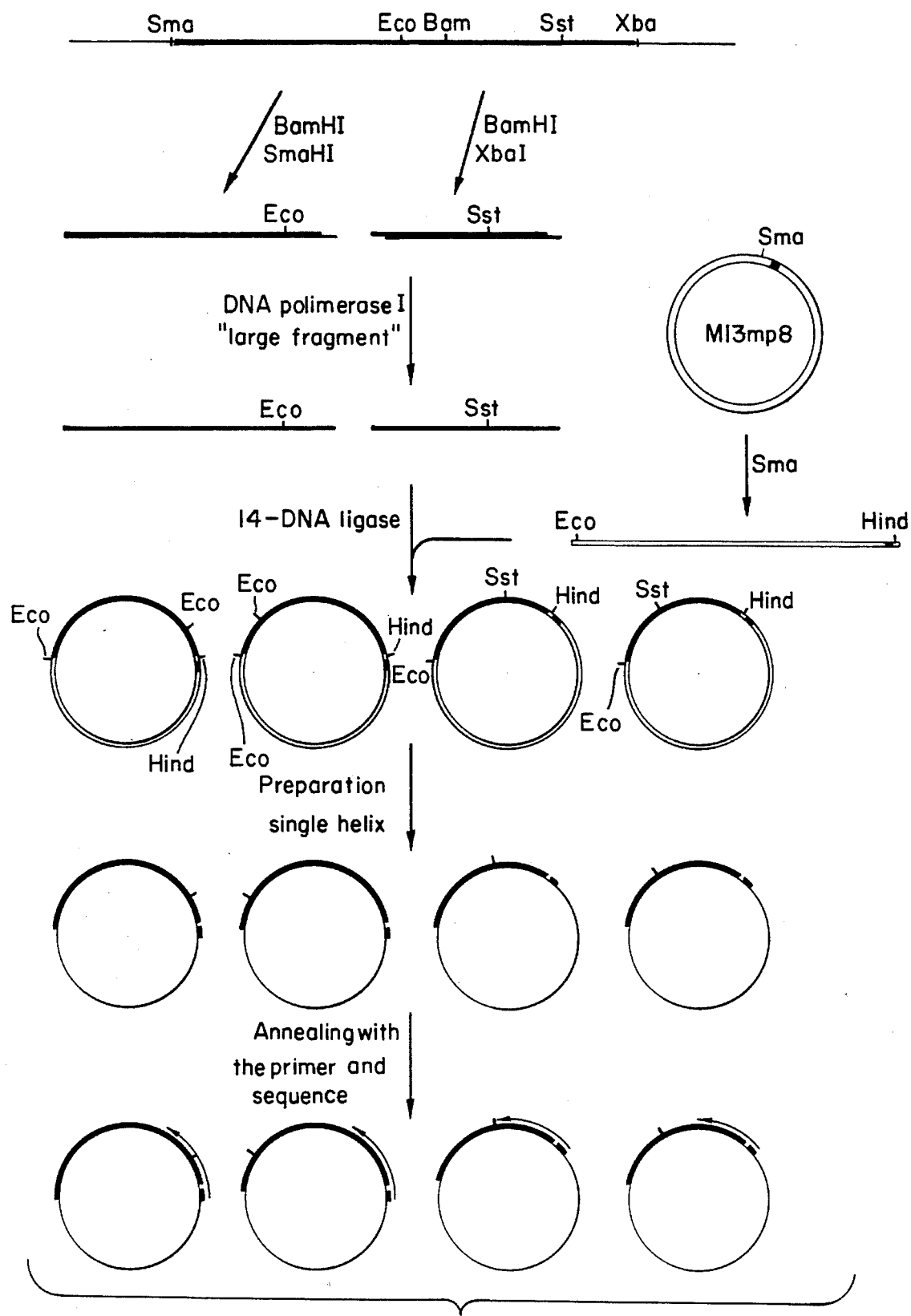

FIG. 6: Diagram of cloning of SmaI-BamHI (1900 bp) and BamHI-XbaI (1300 bp) fragments from plasmid pSM257 in vector M13 mp8.

FIG. 7: Nucleotide sequence of 3335 bp fragment of chromosomal DNA from Pseudomonas SMP1 containing the isoamylase gene.

FIG. 8: Nucleotide sequence of the coding structural gene for isoamylase which is formed from 2250 bp and the amino acid sequence of the enzyme derived from the nucleotide sequence (750 amino acids).

FIG. 9: Nucleotide sequence of the fragment of chomosomal DNA obtained from Pseudomonas SMP1 containing the structural gene of isoamylase and the regulation and secretion sequences.

The coding fragment for isoamylase and the signal sequence (LS) thereof comprising 2328 bp and codes for a protein containing 776 amino acids.

In the sequence, the following symbols are used:

 = promoter

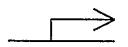 = presumed transcription site

RBS= ribosome recognition site

LS= signal sequence

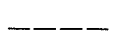 = structural gene of isoamylase

-continued

——— = terminator sequence

Figure 10:
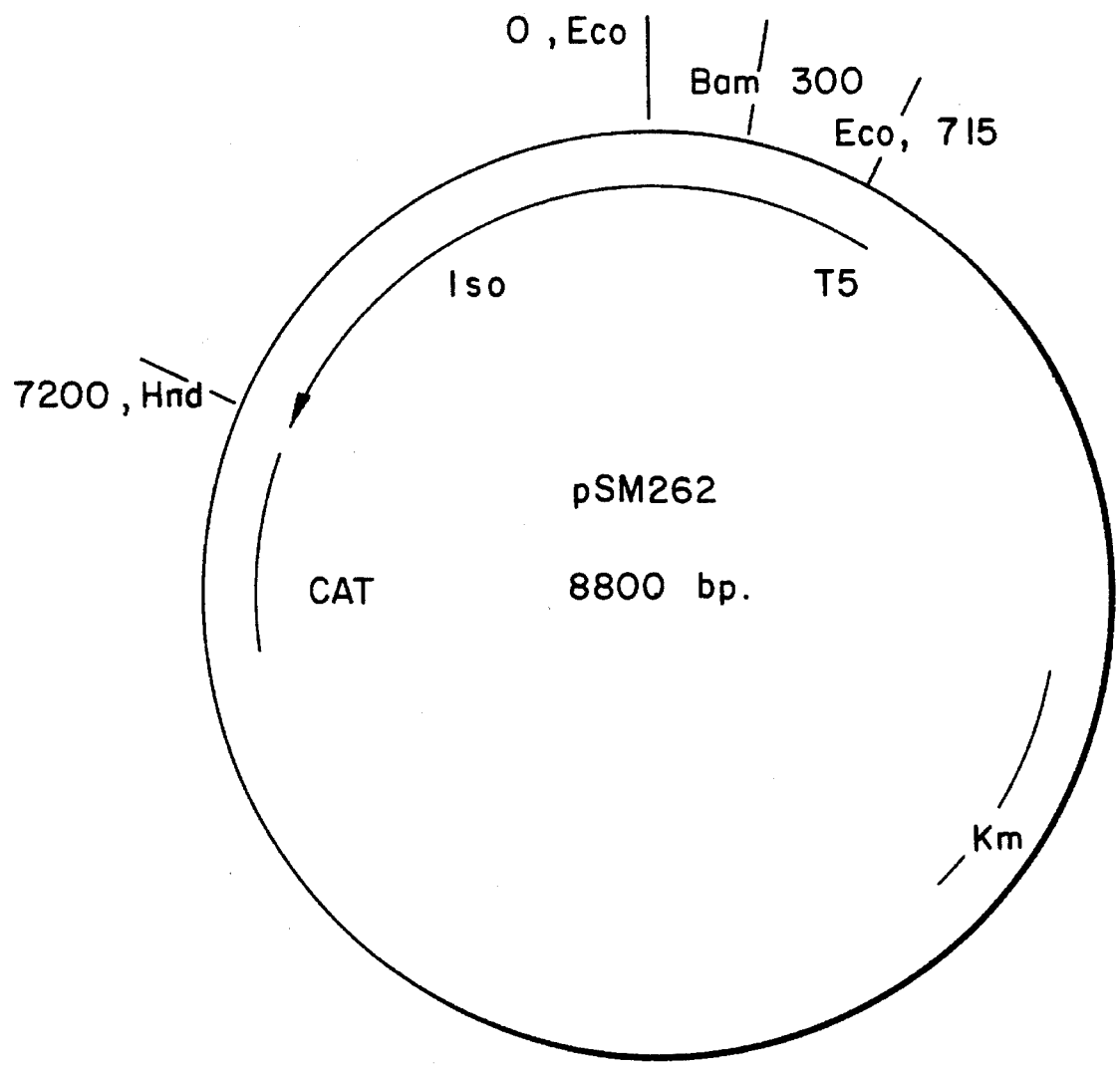

FIG. 10: Restriction map of plasmid pSM 262.

Figure 11:
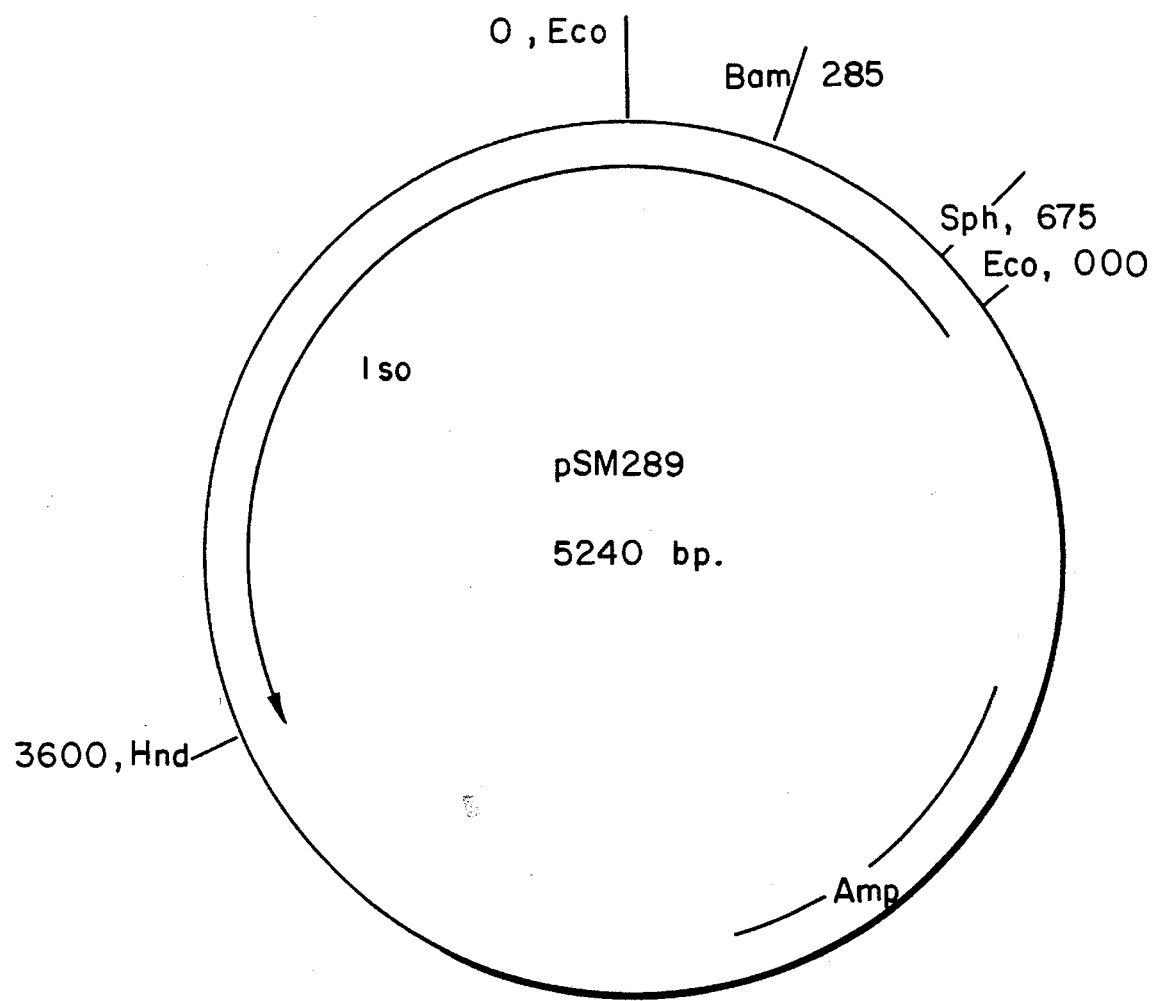

FIG. 11: Restriction map of hybrid plasmid pSM289 for expression and secretion in *Escherichia coli*.

Figure 12:
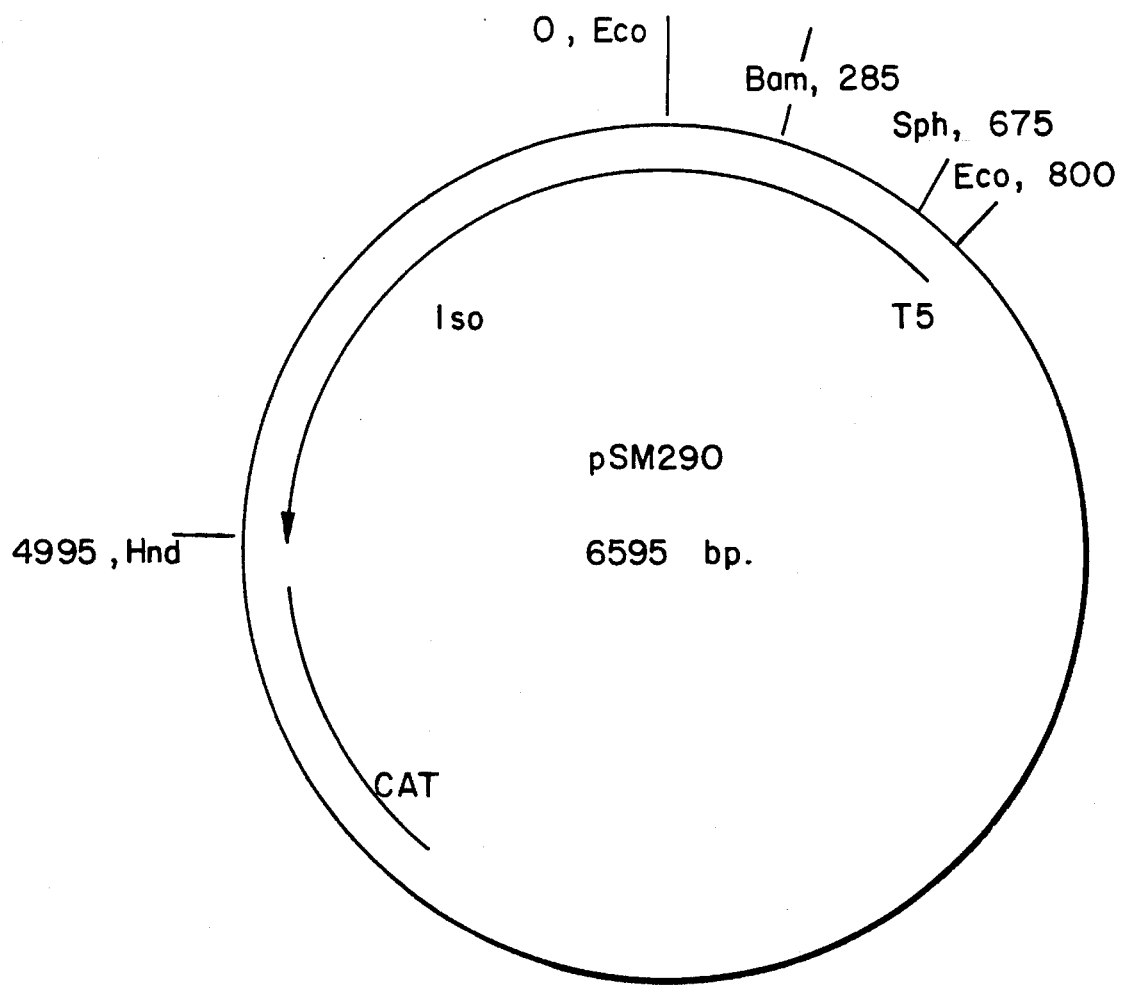

FIG. 12: Restriction map of hybrid plasmid pSM290 for expression and secretion in *Bacillus subtilis*.

According to the invention, any species of the genus Pseudomonas capable of producing isoamylase can be used for isolating the coding gene for the aforementioned enzyme.

Preferably use was made of a strain of Pseudomonas (Pseudomonas SMPI) isolated in our laboratory and capable of producing high yields (about 125 U/ml) of an isoamylase having good activity and thermal stability, The strain was analyzed by the techniques of Kado and Liu (1981) (J. of Bacteriol. 145, 1365) in order to check whether the isoamylase gene was present in its chromosome or in a plasmid. The results showed that the strain in question did not have non-chromosomal forms of DNA.

Consequently, according to the invention, the gene from isoamylase was isolated by constructing genome banks of Pseudomonas SMPI by using suitable restriction enzymes for digesting chromosomal DNA thereof.

More particularly two genome banks of Pseudomonas SMPI were constructed by digesting the chromosomal DNA extracted from the micro-organism, separately with EcoRI (BRL) and Sau3A (BRL) restriction enzymes. The reaction was carried out in a buffer solution at a temperature of or about 37° C. for sufficient time to obtain the desired digestion.

Out of the resulting fragments of DNA, those were purified which had dimensions between 3000 and 4000 base pairs (bp).

The choice was dictated by the fact that, since the molecular weight of isoamylase was known, the size of its gene could be estimated as around 3000 to 4000 bp.

The resulting two populations of fragments of EcoRI and Sau3A DNA were then inserted into a cloning vector for expression in *Escherichia coli* (*E. coli*), under conditions suitable for condensing a single fragment of DNA per molecule of vector.

More particularly the reaction was carried out in a buffer solution in the presence of the T4DNA ligase enzyme (BRL) at a temperature between 4° C. and 37° C., preferably between 13° and 18° C.

Vectors suitable for the purpose can be chosen from *E. coli* plasmids or bacteriophages normally used in the known art.

More particularly use was made of plasmid pUC12 (1800 bp) described by Messing J. et al. ((1982) Gene 19, 159) which is an easy and quick method of distinguishing those clones which have incorporated a fragment of extraneous DNA.

The plasmid does in fact carry genes for β-lactamase and β-galactoxidase, and thus enables the host strain of *E. coli* to grow on a medium containing ampicillin. When an extraneous fragment is inserted between the restriction sites present on the gene for β-galactoxidase, which are particularly suitable for cloning, the gene is broken and no longer able to produce the enzyme.

It is thus possible, by using substances similar to lactose, which dye degraded molecules, to distinguish recombinant clones (not dyed) from clones containing the original plasmid (dyed blue).

According to the invention, the plasmid DNA from pUC12 was made straight-chain by digestion with restriction enzymes which cut inside the nucleotide sequence of β-galactoxidase and, after precipitation and separation from the reaction mixture, was ligated to the fragments of chromosomal DNA of Pseudomonas SMPI previously obtained by digestion with EcoRI and Sau3A.

In order to prevent recyclization of the plasmid, before the ligase reaction, the plasmid DNA molecule was treated with alkaline phosphatase, an enzyme which removes the phosphate group from end 5' of the molecule and prevents condensation of terminal 3'OH in the presence of ligase.

The ligase reaction was brought about by using a plasmid: DNA fragment ratio favourable to the plasmid, preferably 2:1.

At the end of the reaction the two ligase mixtures were used to convert cells of *E. coli* made competent by the method described by Mandel M. and Higa 1970 (J. Mol. Biol. 53, 154), thus obtaining two populations of colonies (genome banks). Each colony carried a hybrid plasmid comprising plasmid pUC12 and a fragment of chromosomal DNA of Pseudomonas SMPI.

Cells of *E. coli* suitable for the purpose can be chosen from

*E. coli* JM 83 (pro, ara, Δ lacpro, straA, φ 8Od, lacZ M15), *E. coli* HB101 (F⁻, hsd S20 ($r_B^-$, $m_B^-$) rec A13, ara-14, proA$_2$, Lac Y1, galK2, rps L20 (Sm$^R$), Xyl-5, mtl-1, supE44λ), *E. coli* JM 101 (lac, pro, supE, thi F' proAB,lac$^{-q}$) and *E. coli* 71/18 α (lac-proAB), thi, supE, [F', proAB, lacI$^{-q}$ Z M15].

The transformed cells, placed on a medium which had been made selective, were used to isolate the clones containing hybrid plasmids, the pUC12 being transformed with an efficiency greater than 2×10⁶ colonies per λg of DNA.

The resulting genome banks were then analyzed to detect the presence therein of clones bearing the isoamylase gene. This can be done by various methods such as hybridization with specific DNA probes or screening by direct expression.

The first method is mainly based on determining at least part of the amino acid sequence of isoamylase. This information is used to synthesize small nucleotide fragments which, when suitably marked, are used to determine the positive clones, using generally known techniques (Hogness D. S. (1975) P.N.A.S., 72, 3961; Mason P. J. et al. (1985) "Nucleic Acid Hybridization" 245 p IRL PRESS Washington D.C.).

The second method, on the other hand, is based on the assumption that the isoamylase Sere can be expressed from the clone of the genome bank containing it.

If this clone is grown In a medium containing amylopectin, the amylopectin will become degraded and the degradation can be detected by colorimetric methods. According to the invention, therefore, recombinant clones of the two genome banks of Pseudomonas SMPI were assayed by direct expression, using a minimum culture medium containing amylopectin and buffered to pH < 6.0. Degradation of amylopectin due to the presence of the enzyme was subsequently demonstrated with iodine vapours.

This method was used to isolate two clones, both from the Sau3A genome bank, which gave a clear positive response to assay on a plate. The ability of the two clones to produce isoamylase was also confirmed by immunological assay with specific anti-isoamylase antibodies, using the Western-blot technique (Hames B. D. et al. (1981) Gel Electrophoresis of Proteins 290 p. IRL PRESS Washington D.C.).

Next, according to the invention, the restriction map of the hybrid plasmids of the two positive clones was determined.

In practice these plasmids were isolated by using the method of Birnboim H. C. et al ((1979) Nucleic Acids Res. 7 1513) and were analyzed by electrophoresis after treatment with suitable restriction enzymes.

One of the two plasmids (pSM257) had an insert of about 3200 bp which was found to contain an EcoRI restriction site, a BamHI site and a SstI site. The other plasmid (pSM258) contained an insert of about 3000 bp containing the same restriction sites as the first plasmid.

The plasmids were then successively digested with two enzymes which frequently cut and, though of slightly different dimensions, have shown a similar electrophoretic profile.

According to the invention, the nucleotide sequence of chromosomal DNA fragments of about 3200 bp was determined.

This can be done by using the technique of Maxam and Gilbert ((1977) P.N.A.S. 74, 560) using a chemical system for specific degradation of DNA, or the method of Sanger F. et al ((1977) P.N.A.S. 74, 5463), based on a sequencing enzyme system.

The latter method, which is particularly preferred for sequencing of very long and little-known fragments of DNA, requires the fragment to be sequenced to be available in the form of a single helix (template) and a small oligonucleotide (15–20 bases) defined as the primer and complementary to the initial region of the single helix. According to the invention, therefore, the chromosomal DNA fragment of about 3200 bp was sub-cloned in a vector and sequenced by the Sanger method. Viruses, plasmids or bacteriophages can be suitable vectors for the purpose. Use is preferably made of phage vectors M13mp8 (Messing J. et al. (1982) Gene, 19, 263) and M13mp9 (Yamamoto K. R. et al. (1970), Virology, 40, 734) in which the cloning sites are disposed in inverted manner as compared with the annealing site of the primer and can be used to define the sequence of an insert from two opposite ends.

The phage vector M13mp8 is particularly preferred for the object of the invention, since its DNA can be isolated in double helix form when present in the cells of *E. coli*, whereas it is in the form of a single helix when the phage, leaving the bacteria cells at the end of its infective cycle, flows into the supernatant culture medium.

According to the invention, the isoamylase gene was divided into two fragments, each of which was inserted into the phage vector M13mp8.

More particularly, plasmid pSM257 was digested with BamHI, SmaI and XbaI restriction enzymes, taking advantage of the presence of the BamHI site inside the gene and of the other two sites before and behind the gene. The ends of the resulting fragments were flattened by treatment with DNA polymerase I enzyme (large fragment or Klenow fragment) and the fragments were separated by electrophoresis and subsequently eluted by known general methods.

The resulting fragments, containing about 1900 bp (SmaI-BamHI) and about 1300 bp (BamHI-XbaI) respectively, were inserted into M13mp8 phage after it had been made straight-chain by Sinai enzyme in the presence of T4 DNA ligase, and the ligase mixture was then used to transform competent cells of *E. coli*.

After identification of the recombinant clones, i.e. those carrying the hybrid vectors, the orientation of the two fragments was determined by suitable cuts with restriction enzymes.

More particularly the hybrid vector containing the 1900 bp fragment was digested with the EcoRI restriction enzyme which cuts inside the fragment in asymmetrical manner and in the vector in the immediate neighbourhood of the fragment, the result as expected being a segment of 300 bp or 1600 bp depending on the orientation. Similarly, plasmids carrying the 1300 bp fragment, when digested with SstI and HindIII enzymes, gave 500 bp and 800 bp segments, depending on the orientation.

Confirmation of the opposing orientations was also obtained by the method described in Messing J. (1983) Methods in Enzymology, 101, 20. The single helices were then extracted from the clones and sequenced by using the strategy of successive primers described by Strauss E. C. et al. (1986) Analytical Biochem. 154, 353.

The fragment of DNA inserted into plasmid pSM257 was found to contain 3335 bp, whereas the coding region for isoamylase enzyme contained 2328 bp, equal to 776 amino acids.

About 1000 bases from one end of the 3335 bp fragment, a sequence of 54 nucleotides corresponding to the amino terminal sequence of the given enzyme was determined by known methods, using an automatic protein sequencer. This method was used for accurately identifying the 5' terminal of the structural gene of mature isoamylase, which was found to contain 2250 bp, equal to about 750 amino acids.

As expected from a secreted protein, immediately above the structural gene of mature isoamylase, a coding zone was found for a typical signal sequence of 26 amino acids (LS) responsible for secretion of the protein and beginning with a methionine (-ATG-). This LS is characterised by a highly hydrophobic structure necessary for conveying the protein outside the cell membrane. The LS is removed by a membrane peptidase after translocation of the protein, and the recognition site of the peptidase is identifiable in the Ala-His-Ala sequence and the cut is made after the second alanine.

This was confirmed by the aminoterminal sequence data of the secreted protein purified by us, the sequence being Ala-Ile-Asn.

Ten nucleotides before the -ATG- initiating the translation, we also found a typical bond site for ribosomes (RBS) having the sequence-GGAGG.

About 130 nucleotides above LS, a structure (-GGATGT) was identified similar to the "consensus sequence" (-GGATGA-) of promotors sensitive to induction by maltose.

35 nucleotides in front of this sequence there is -G- residue which might be identified as the begining of transcription.

10 nucleotides before this -G- there is a -TCTATT- structure closely similar to the analogous "–10 region of pullulanase, a gene which is induced by maltose (Chapan C. et al. (1985) J. of Bacteriol 164, (2), 639). Behind the gene, about 10 nucleotides after the STOP -TAG- codon, there is a typical transcription terminator structure comprising a repeated inverted sequence separated by a zone of four nucleotides capable of forming a secondary structure having a $\Delta G$ of formation of $-24.8$ Kcal/mol calculated in accordance with the method of Tinoco et al. ((1973) Nature New Biol. 246, 40).

According to the invention, and on the basis of the sequence data given hereinbefore, the DNA fragment containing the coding gene for isoamylase or regions thereof can be used to construct molecules of recombinant DNA for producing isoamylase or polypeptides having a biological activity equivalent to that of isoamylase, using replicable cloning vectors such as plasmids.

In one embodiment of the invention, the coding structural gene for mature isoamylase can be inserted into a plasmid vector by positioning it behind a promotor and a secretion sequence different from the Pseudomonas sequences. This purpose can be served by strong promotors, i.e. capable of very efficiently guiding the expression of the gene behind them, and chosen from among the promotors known in the art.

Examples of such promotors are those in the triptophan system (trp), the lactose system (lac) or bacteriophages such as P1 and T5.

However, numerous other microbial promotors have been identified and used, and details of the sequences thereof have been published by Siebenlist et al. Cell., 20, 269 (1980).

Coding nucleotide sequences for a secretion-signal protein can be chosen from among those generally used in the art of recombinant DNA.

Subtilisin and neutral protease are examples of sequences suitable for the purposes of the invention.

According to another embodiment of the invention, molecules of recombinant DNA can be constructed by positioning the coding gene for isoamylase, without the regulating sequences, in a plasmid vector under the control of regulating sequences different from Pseudomonas sequences.

The molecules of recombinant DNA obtained by working in accordance with either of the previously-described embodiments are then used to transform host organisms, usually selected from bacteria and yeasts and made competent by one of the methods described in the art.

The thus-transformed micro-organisms are used in fermentation processes for producing isoamylase or polypeptides having isoamylase activity.

Preferably use is made of micro-organisms chosen from the group comprising E.coli K12, Bacilli and Saccharomyces.

Among these, strains of *Bacillus subtilis* are particularly preferred, both because their lack of pathogenicity to man and because of their capacity to secrete the synthesized heterologous protein directly in the culture medium.

This can advantageously simplify the subsequent operations of recovering and purifying the desired protein.

In a preferred embodiment of the invention, molecules of recombinant DNA for expression of isoamylase in *E.coli* and *B. subtilis* were constructed by inserting a DNA fragment containing the LS and the structural gene of isoamylase into cloning vectors which were replicable in the aforementioned bacteria.

More particularly, owing to the presence of the NarI restriction site immediately in front of the isoamylase RBS, it has been possible to isolate a DNA fragment of about 2400 bp from plasmid pSM257, the fragment containing the coding sequence for the secretion-signal peptide and for mature isoamylase without the original promotor of Pseudomonas SMPI.

The fragment was introduced, after constructing intermediate plasmids as described in Example 4, into the pUC12 cloning vector for expression in *E.coli*.

The isolated molecule of recombinant DNA was given the symbol pSM289 and used to transform cells of *E.coli* DH1.

These cultivated cells, either on a plate or in a specific liquid medium, were able to express and secrete isoamylase (as shown by the data in Example 6).

According to the invention, the DNA fragment containing the structural gene of isoamylase with its LS was taken from the hybrid plasmid pSM289 as the EcoRI-Hind III fragment and inserted into a cloning vector for expression and replication in *B. substilis*.

To this end, use was made of plasmid pSM268, the construction of which is described in Example 5 hereinafter, and which contains the origin of replication in *B. subtilis*, the coding gene for resistance to chloramphenicol and a strong synthetic promotor, of the phage. The EcoRI-HindIII fragment was positioned under the control of the aforementioned strong promotor and the resulting molecule of recombinant DNA (pSM290) was isolated and described.

Accordingly the junction region between the isoamylase gene and the promotor has been sequenced in order to check that no rearrangement of the sequence had occurred during the cloning operation.

The results showed the expected sequence.

Cells of *B. subtilis* made competent by the method of Dubnau D., and Davidoff-Abelson R. (1971) (J. Mol. Biol. 56:209) were then transformed with pSM290.

According to the invention, use can be made of different strains of *B. subtilis* filed at various collecting centres and available to the public.

More particularly, use was made of the strain MS108 Bacillus subtilis (rec$^-$, Lis$^-$, leu$^-$) and the transforming substances were selected on a suitable culture medium, e.g. VY plus chloramphenicol.

The positive clones were then cultivated on plates of M9 and MB medium and in the liquid media, at a temperature of or about 37° C. for 16 hours.

At the end of this period, the isoamylase in the culture medium and the cell extract was determined by the method of Yokobayashi A. et al. (1970) Biochem. Biophis. Acta 212:458–469).

As the results show, these micro-organisms were capable not only of expressing the isoamylase enzyme but also of secreting it in quantities comparable to those obtained with the original strain, Pseudomonas SMPI.

It was also found that, whereas in the case of Pseudomonas SMPI, optimum production of isoamylase is obtained about 72–120 hours after incubation, only 16 hours were required for *B. subtilis* (pSM290).

The hybrid plasmid pSM257 (*E. coli*) 71/18 (pSM257) and the strain Pseudomonas SMPI were filed at the American Type Culture Collection on Jul. 24, 1987 and given the accession numbers ATCC 67474 and ATCC 53651 respectively.

The following experimental examples non-limitatively illustrate the invention.

Example 1

Extraction of chromosomal DNA from Pseudomonas SMPI 100 ml of HSM fermentation medium (20 g/l maltose, 4g/l Na glutamate, 1.5 g/l $(NH_4)_2 HPO_4$, 1 g.l $KH_2PO_4$, 0.5 g/l $MgSO_4.7H_2O$, 0.1 g/l $FeCol_3.6H_2O$, 0.1 g/l $MnCl_2.4H_2O$ and 0.1 g/l NaCl, pH 5.5) were inoculated with the strain Pseudomonas SMPI and kept under agitation (220 rpm) at 30° C. for 5 days. At the end of this period the cells were separated from the culture broth by centrifuging (10 minutes, 5000 rpm) in a Sorvall RC-5B centrifuge, Model SS34 at 4° C., washed (2×120 ml) with a solution of 25% saccharose, 100 mM NaCl and 50 mM Tris-HCl pH 7.5, recentrifuged under the same conditions as hereinbefore and resuspended in 10 ml of buffer solution (100 mM EDTA and 50 mM NaCl, pH 6.9) containing 1 mg/ml of lysozyme (SIGMA), The resulting suspension was kept at 37° C. for 30 minutes with gentle agitation, and was then mixed with 1 ml of 10% SDS (sodium dodecyl sulphate) and kept at 60°for 10 minutes, and with 1 mg/ml of pronase preincubated at 37° C. for 30 minutes in 1×SSC (1×SSC=

0.15M NaCl and 15 mM sodium citrate) and kept at 37° C. for 2 hours. After NaCl had been added to a final concentration of 1M, the DNA was precipitated with 2 or 3 volumes of cold ethanol (−20° C.), collected with a glass rod and resuspended in 10 ml of 0.1×SSC. The suspension was kept under gentle agitation at ambient temperature (20°–25° C.) overnight and, after adding RNAse (10 μg/ml), at 37° C. for 30 minutes. The salt concentration of the solution was then brought to 1×SSC. After extracting the protein with phenol (1 volume) the DNA was precipitated by dropwise adding isopropanol to the solution, which was kept under gentle agitation at ambient temperature.

The DNA was then recovered by centrifuging and resuspended in 1 ml of 0.1×SSC.

The resulting quantity of chromosomal DNA, evaluated by spectrophotometric recording at OD260 using a Perkin-Elmer mod. 515 spectrophotometer, was 0.645 mg/ml.

Example 2

Cloning the isoamylase gene
a) Preparation of the Pseudomonas SMPI genome bank in EcoRI 80 μg of chromosomal DNA obtained as described in Example 1 hereinbefore were suspended in 800μl of buffer (Tris-HCl 100 mM, NaCl 50 mM and MgCl$_2$ 10 mM, pH 7.5) and incubated at 37° C. for 2.5 hours in the presence of 375 units (U) of EcoRI (BRL) enzyme.

The DNA mixture was then loaded on a saccharose gradient (10–40%) and centrifuged (20 hours, 25000 rpm) in a Beckman sw 28 rotor at 20° C.

The gradient was then divided into fractions and a portion of each fraction was analyzed by electrophoresis on 0.7% agarose gel at 20 V overnight, in order to identify the fractions containing fragments having the desired dimensions (3000–4000 bp). These fractions were collected and the DNA was precipitated with ethanol at -20° C. and separated by centrifuging at 12000 rpm for 15 minutes. The DNA was then inserted into plasmid pUC12 from *E. coli*, previously digested with EcoRI.

7 μg of pUC12 (2800 bp) were digested with 10 U of EcoRI (BRL) enzyme in 70 μl reaction mixture having the previously-stated composition at 37° C. for 1 hour.

The plasmid DNA was then precipitated with ethanol at −20°, separated by centrifuging (15 minutes, 12000 rpm) in an EPPENDORF centrifuge at 4° C., resuspended in 50 μl of TE buffer (10 mM Tris-HCl (pH 8.0) and 1 mM EDTA) and subjected to treatment with 1 U of CIP (Calf intestinal phosphatase) enzyme (Boehringer) for 30 minutes at 37° C.

The enzyme reaction was then stopped by adding to the solution 40 μl of H$_2$O, 10 μl of 10×STE (100 mM Tris-HCl, 1 m NaCl, 10 mM EDTA, pH 8) and 5 μl of 10% sodium dodecyl sulphate (SDS).

2.6 μg of the plasmid precipitated as previously described were incubated with 1.3 μg of the mixture from the gradient containing the 3000–4000 bp DNA fragments, for 12 hours at 14° C. in the presence of 20 U of T4DNA ligase (Boehringer) in a final volume of 130 μl of buffer (66 mM Tris-HCl, 1 mM ATP, 10 mM MgCl$_2$ and 10 mM dithiothreitol pH 7.6).

2 μl portions of the ligase mixture were used to transform 300 μl of *E. coli* 71/18 cells (Miller J. H. (1972) Experiments in Molecular genetics Cold Spring Harbor Lab. New York) made competent by treatment with 50 mM CaCl$_2$ (Mandel M and Higa (1970) J. Mol. Biol. 53, 154).

The transformants were then selected by placing the cells on 2×YT medium (16 g/l Bacto Tryptone (DIFCO), 10 g/l Bacto-yeast extract (DIFCO) and 10 g/l NaCl) made selective by adding 50 μg/ml ampicillin, 0.05 mM IPTG (isopropyl β-D-thiogalactopyranoside) and 0.2% X-Gal( 5-bromo-4-chloro-3-indolyl-D-galactopyranoside) and incubated for 12 hours at 37° C. in a thermostatically controlled chamber.

From the entire mixture of ligase, 6000 recombinant colonies were obtained.

The colonies were transferred in groups of 100 on to plates of Luria agar medium (Bacto-tryptone, 5 g/l Bacto yeast extract and 5 g/l NaCl) containing 50 μg/ml ampicillin.
b) Preparation of the genome bank of Pseudomonas SMPI in Sau3A 78 μg of Pseudomonas SMPI chromosomal DNA were partially digested with 16 U of enzyme Sau3A (BRL) in 100 μl of reaction buffer (6 mM Tris-HCl pH 7.5, 50 mM NaCl and 5 mM MgCl$_2$) at 37° for 30 minutes.

The thus-digested DNA mixture was then loaded on a saccharose gradient and the fractions containing DNA fragments containing from 3000 to 4000 base pairs were identified by electrophoresis on agar gel. The experimental conditions were identical with those given in Part a).

7 μg of pUC12 were digested in 70 μl of reaction mixture (10 mM Tris-HCl pH 8.0, 100 mM NaCl and 5 mM MgCl$_2$) with 50 U of MamHI (BRL) enzyme at 37° C. for 2 hours.

The plasmid DNA was then precipitated with ethanol at −20° C., centrifuged and treated with CIP (Calf intestinal phosphatase) enzyme to prevent recyclization thereof as described in Part a). 160 ng of DNA were then incubated with 80 ng of mixture from the gradient containing the 3000–4000 bp fragments for 18 hours at 4° C. in 100 μl of the reaction mixture in the presence of 10 U of T4DNA ligase.

2 μl portions of the ligase mixture were then used to transform 300 μl of cells of *E. coli* 71/18 made competent by the method stated hereinbefore and were then placed on 2×YT agar medium and incubated at 37° for 12 hours.

From the entire ligase mixture, 6300 recombinant colonies were obtained.

The colonies were transferred in groups of 100 on to plates of Luria agar medium (Bacto-tryptone, 5 g/l Bacto yeast extract, 5 g/l NaCl) containing 50 μg/ml ampicillin.
c) Screening by direct expression of the EcoRI and Sau3A genome banks The colonies from the EcoRI and Sau3A genome banks were transferred by replica plating (Hayes W. 1968, The genetics of bacteria and their viruses 187 p. Wiley, New York) on to plates of M9+glucose minimum medium (6 g/l Na$_2$HPO$_4$, 3 g/l KH$_2$PO$_4$, 0.5 g/l NaCl, 1 g/l NH$_4$Cl, 2 mM MgSO$_4$, 0.1 mM CaCl$_2$, 0.2% glucose, 0.5% agar and 1% amylopectin, pH 6.0) and incubated at 37° C. for 48 hours.

The colonies were then exposed to iodine vapours for 1–2 minutes, using a solution having the following composition:

| Iodine flakes | 2 g |
| KI | 1 g |
| EtOH 95% | 25 ml |
| H$_2$O | 75 ml |

(Harada T. et al. (1974), Appl Microbiol. 28, 336). The colonies coming from the EcoRI genome bank gave a negative result, whereas two clones, called 9 and 17, from the Sau3A genome bank showed an amylopectin degradation ring (FIG. 1) identical with that observed in the case of Pseudomonas SMPI grown under the same conditions. This indicated the capacity of these clones to produce isoamylase, and consequently the presence of the coding gene for the aforementioned enzyme inside the clones.

Non-transformed *E. coli* 71/18 cells were grown as a control on M9+amylopectin minimum medium, pH 6.0 at 37° C. for 48 hours and subjected to iodine vapour, but did not show a degradation ring.

It was also found that clones 9 and 17 when grown on minimum medium at other pH values did not show any degradation ring at pH >6.0.

d) Analysis by restriction of positive clones

The recombinant plasmids present in clones 9 and 17 were then isolated by large-scale extraction and analyzed by electrophoresis on 0.8% agarose gel at 100 V for 2 hours after treatment with the following restriction enzymes: PstI, EcoRI, HindIII, SstI, SmaI, BamHI, XbaI and SalI.

Plasmid pSM257 isolated from clone 9 contained an insert of about 3200 bp which was found to contain an EcoRI site, a BamHI site and an SstI site, the exact positions of which are shown in FIG. 2.

Plasmid pSM258, isolated from clone 17, had an insert of about 3000 bp which was found to contain the same restriction sites as plasmid pSN257.

The restriction map of this plasmid is given in FIG. 3.

The two plasmids were then digested with two frequently cutting enzymes such as Sau3A and HpaII and compared with plasmid pUC12 treated with the same enzymes and with molecular weight markers (Boehringer).

Analysis on polyacrylamide of the resulting digested hybrid plasmids showed an electrophoretic profile similar in each case but different from that obtained on pUC12 (FIG. 4).

e) Analysis by "Western-blot"

Cells from clones 9 and 7 were taken from plates of M9-amylopectin (pH 6) medium and dissolved in 10 µl of STS buffer (125 mM Tris-HCl, 3% 2-mercaptoethanol, 3% sodium dodecyl sulphate and 20% glycerol, pH 6.8).

The solutions were then loaded on to discontinuous polyacrylamide-STS gel (Hames B. D. et al (1981) Gel Electrophoresis of Proteins, 290 IRL Press Washington D.C.) and subjected to 125 V for 2 hours.

The proteins were then transferred from the gel on to Schleicher and "low melting" nitrocellulose filters by the method described by Parker R. G. et al ((1980), Methods Enzymology 65, 358).

Simultaneously 2 µg of M13mp8 were digested in 30 µl of mixture with 10 U of Sinai restriction enzyme at 25° C. for 1.5 hours.

10 ng of each fragment were then ligated with 200 ng of M13mp8 phage DNA in 50 µl of ligase mixture in the presence of 1 U of T4DNA ligase at 23° C. for 18 hours.

All the ligase mixtures were then used to transform competent cells of *E. coli* 71/18 and the recombinant clones were selected on L agar plates.

The clones containing hybrid phage vectors were then analysed to determine the orientation of the fragments by suitable cuts with restriction enzymes.

When for example the hybrid vector carrying the 1900 bp fragment was digested with the EcoRI restriction enzyme which cuts asymmetrically in the fragment and in the vector in the immediate neighbourhood of the fragment, the result depending on the orientation was a 300 bp or a 1600 bp fragment. Similarly, when plasmids carrying the 1300 bp fragment were digested with enzymes SstI and HindIII, the result was Schull 45 µm fragments and filters treated with antiisoamylase antibodies and rabbit anti-IgG antibodies conjugated with peroxidase (Miles) as reported by H. Towbin et al. ((1979) PNAS USA Vol. 76, 4350–4354).

The results, given in FIG. 5, show a positive signal, i.e. a specific reaction of the protein with the anti-isoamylase antibodies.

Example 3

Cloning of the approx. 3200 bp chromosomal DNA fragment in M13mp8 and sequencing thereof 5.2 µg of plasmid pSM257 were digested in 20 µl of buffer containing 10 U of SmaI (BRL) enzyme at 25° C. for 1 hour and, after the reaction volume had been brought to 15 µl with 10 U of BamHI (BRL) at 37° C. for 1 hour. 2.6 µg of plasmid pSM257 were digested with 10 U of BamHI and XbaI (BRL) respectively in 50 µl of buffer at 37° C. for 2 hours, The enzyme reactions were inactivated at 65° C. for 10 minutes and the resulting DNA fragments were treated with 2 U of DNA polymerase I enzyme (large fragment or Klenow Fragment) in order to flatten the ends thereof.

Fragments SmaI-BamHI of approximately 1900 bp and BamHI-XbaI of approximately 1300 bp were then separated by means of electrophoresis on "low melting" agarose gel according to the method described by Parker, R. G. et al. ((1980), Methods Enzymology, 65, 358).

At the same time, 2 µg of M13mp8 were digested in 30 µl of mixture with 10 U of restriction enzyme SmaI at 25° C. for 1.5 hours.

Then 100 ng of each fragment were ligated with 200 ng of phagic DNA M13mp8 in 50 µl of ligase mixture in the presence of 1 U T4 DNA ligase at 23° C. for 18 hours.

The whole ligase mixtures were then used to convert competent cells of *E. coli* 71/18 and the recombinant clones were selected on L agar plates.

The clones containing the hybrid phagic vectors were successively analyzed to determine the orientation of said fragments by means of appropriate cuts with restriction enzymes. Thus, digesting the hybrid vector carrying the fragment of 1900 bp with the restriction enzyme EcoRI, which cuts inside the fragment asymmetrically and in the vectors in the immediate vicinity of the fragment itself, a fragment of 300 bp or of 1600 bp appeared, depending on the orientation. Similarly, the plasmids carrying the fragment of 1300 bp, when digested with enzymes SstI and HindIII, gave rise to fragments of 500 bp and 800 bp, depending on the orientation. The plasmids containing the two fragments, oriented in the two possible ways, were called alpha, beta, gamma and delta (FIG. 6).

Confirmation of the opposite orientations was subsequently obtained by the method described by Messing ((1983) Methods in Enzymology, 101, 20).

The single helices were then sequenced by the method of Sanger F. et al ((1977) P.N.A.S. 74, 5463) using the strategy of successive primers described by Strauss et al. (Anal. Biochem. 154, 353 (1986)). The oligonucleotides used as primers were synthesized by means of the automatic System 1 Plus DNA Synthesizer (Beckman).

The sequencing reactions were carried out in accordance with the normal procedure using the "DNA sequencing system (NEN)" kit containing $\alpha[^{32}P]$ dATP as tracer.

The apparatus used for electrophoretic separation was the Macrophor sequencing system (LKB).

There are some problems connected with the nucleotide sequence of the isoamylase Mane which might result in anomalous migration of the fragments on gel. These were avoided by using the technique described by Mizusaw S. et al. ((1986) Nucleic Acids Reser. 14 (3) 1319), using an analogue of guanosine, i.e. C7 deaza dGTP which is without a nitrogen atom in position 7 and consequently greatly reduces the capacity of the nucleotide to form secondary structures with adjacent nucleotides. Another method of clarifying some complex areas of the sequence is to use the inverse transcritase enzyme instead of DNA polymerase I (large fragment).

The resulting sequenced fragment of chromosomal DNA of Pseudomonas SMPI contains 3335 base pairs, whereas the region coded by the enzyme contained 2328 bp, equal to 776 amino acids (FIGS. 7–8).

FIG. 9 gives the nucleotide sequence of the structural gene of isoamylase, with the possible gene regulating sequences.

The amino acid composition of the protein deduced from the nucleotide composition, the sequence for which is shown in FIG. 9, is given in Table I hereinafter, showing marked hydrophobic characteristics due to the presence of 30% of saturated aromatic and aliphatic radicals.

TABLE I

| No. of radicals, % of total | | | No. of radicals, % of total | |
|---|---|---|---|---|
| Ala | 86 | (11.1) | Leu | 49 | (6.3) |
| Arg | 26 | (3.4) | Lys | 14 | (1.8) |
| Asn | 29 | (7.6) | Met | 13 | (1.7) |
| Asp | 42 | (5.4) | Phe | 27 | (3.5) |
| Cys | 8 | (1.0) | Pro | 37 | (4.8) |
| Gln | 36 | (4.6) | Ser | 76 | (9.8) |
| Glu | 18 | (2.3) | Thr | 58 | (7.5) |
| Gly | 78 | (10.1) | Trp | 22 | (2.8) |
| His | 6 | (0.8) | Tyr | 52 | (6.7) |
| Ile | 25 | (3.2) | Val | 44 | (5.7) |
| End | 0 | (0.0) | | | |
| Acids (Asp—Glu) | | | 60 | (7.7) |
| Basic substances (Arg—Lys) | | | 40 | (5.2) |
| Aromatics (Phe—Trp—Try) | | | 101 | (13.0) |
| Hydrophobic substances (aromatics + Ile + Leu + Met + val) | | | 232 | (29.9) |
| Molecular weight 23668 | | | | |

Example 4

Construction of the pSM289 recombinant DNA molecule for expression and secretion in *E. coli*

A) Construction of plasmid pSM221

5 µg of plasmid pUC12 were digested with EcoRI and HindIII (BRL) restriction enzymes by the method suggested by the supplying firm, so as to isolate and separate the polylinker from the aforementioned plasmid.

The plasmid DNA, free from the EcoRI HindIII fragment, was then ligated with a synthetic oligonucleotide containing 18 base pairs and having the following sequence:

```
                AATTCAGCATGCTACCCGGGAA
     Ecori      GTCGTACGATGGGCCCTTTCGA      Hind III
                ─────────────────────
                  Sph I          Ava I
                                 Hpa II
``` in which the ends contain the EcoRI and HindIII sites and the SphI and AvaI sites are in the middle.

B) Construction of plasmid pSM262

5 µg of plasmid pSM257 were digested with 20 U of the restriction enzymes SphI and SmaI (BRL), operating by the method suggested by the supplying firm.

The digestion mixture, after treatment at 65° C. for 10 minutes to block the enzyme reaction, was loaded on 5% acrylamide gel in order to elute the approx. 2400 bp SphI-SmaI fragment containing the isoamylase gene.

1 µg of the fragment was then inserted into plasmid pSM221 (1 µg) previously digested with AvaI enzyme treated with the Klenow fragment of DNA polymerase I in order to obtain compatibility with the SmaI end of the insert and finally with the restriction enzyme SphI.

The ligase reaction between the SphI-SmaI fragment and the thus-digested plasmid pSM221 was carried out in a ligase buffer (50 µl) in the presence of 1 U of T4 DNA ligase at 14° C. for 18 hours. At the end of the reaction, 10 µl of the ligase mixture were used to transform 200 µl of *E. coli* 71/18 cells made competent by treatment with 50 mM CaCl$_2$.

The cells were spread on 2×YT medium (16 g/l bactotryptone, 10 gr/l bacto yeast extract, 1- gr/l NaCl) made selective by adding 50 mg/l ampicillin, 0.05 mM IPTG (isopropyl-D-thiogalactopyranoside) and 0.02% X-gal (5-bromo-4-chloro-3-indolyl-D-galactopyranoside) and incubated for 12 hours at 37° C. in a thermostat. The recombinant plasmids, extracted by the method of Birnboim H. C. and Doly, J. (Nucleic Acids Res. (1979) 7:1513) were subjected to analysis by restriction.

A good percentage of the clones were found to possess the desired fragment inserted in the expected manner.

One of these plasmids, called pSM262, is characterised by the map given in FIG. 10.

C) Construction of plasmid pSM289

10 µg of plasmid pSM257 were digested with 40 U of NarI (BRL) restriction enzyme at 37° C. for 1 hour and then reacted with I "Klenow" DNA polymerase in a final volume of 100 µl of specific buffer for 30 minutes at ambient temperature (20°–25° C.) in order to flatten the ends thereof.

The mixture was then digested with 40 U of BamHI restriction enzyme at 37° C. for 1 hour and loaded on 5% acrylamide gel in order to elute the 511 bp NarI-BamHI fragment (a) containing the leader sequence and the first 390 nucleotides of the structural gene of isoamylase.

The remaining part, 2010 bp of the gene (b) was obtained by digesting plasmid pSM262 (5 µg) with 20 U of BamHI and 20 U of HindIII (BRL) restriction enzymes.

At the same time, 5 µg of vector PUC12 (c) were digested, firstly with 20 U of Sinai restriction enzyme at 25° C. for 1 hour in a buffer recommended by the supplying firm and, after the concentration of salts had been modified by adding NaCl up to a final concentration of 50 mM, the vector was digested with 20 U of HindIII restriction enzyme at 37° C. for 1 hour.

100 ng of vector (c), 100 ng of insert (b) and 35 ng of insert (a) were reacted in a final volume of 50 µl ligase buffer in the presence of 1 U of T4 DNA ligase at 14° C. overnight.

At the end of the reaction, 10 ng of the ligation mixture were used to transform 100 µl of *E. coli* DHI cells (F– rec Al emd Al gyr A96, thi–1, sup E44, hsd R 17 ($r_n^-$, $m_k^-$) made competent with rubidium chloride as described by Hanahan (1983 J. Mol. Biol. 162, 557–580), The transformants were then selected on plates of 2X YT medium at 37° C. for 18 hours. The recombinant plasmid was extracted from a transforming clone and showed the expected pattern after analysis by restriction.

The map of this recombinant plasmid, called pSM289, is given in FIG. 11.

Example 5

Construction of the pSM290 molecule of recombinant DNA for expression and secretion in *B. subtilis*

A) Construction of plasmid pSM268

3 portions each of 1 µg of pSM214 ATCC 67320 were digested with 5 U of BgIII and 5 of BamHI at 37° C. for 1 hour.

The ends of the resulting DNA fragment were eroded by incubating it with 0.3 U of nuclease Ba131 at 23° C. for 2, 3 and 4 minutes and subsequently repaired with DNA polymerase I-large fragment under standard conditions, The resulting molecules, of variable length, were recyclised by treatment with T4 DNA ligase at 14° C. overnight.

The ligation mixtures were then used to transform the SMS108 strain of B. subtilis (rec–, his–, leu–) made competent by the method described by Dubnau D. Davidoff-Abelson R. (1971 ) (J. Mol Biol. 56:209).

The transformants were then selected on VY plates (25 g/l veal infusion broth, 5 g/l yeast extract) containing 5 μg/ml chloramphenicol.

The plasmid extracted from the resulting clones were analyzed by restriction with various enzymes.

The recombinant plasmid, called pSM268, was the smallest (about 5000 bp) of those containing both the origin of replication of B. subtilis and the gene controlling resistance to chloramphenicol antibiotic (the CAT gene ).

10 μg of the aforementioned plasmid were digested at 37° C. for 1 hours with 4 U of each of the following restriction enzymes: EcoRI and HindIII.

After blocking the enzyme reaction at 65° C. for 10 minutes, the digestion mixture was loaded on to "low melting" agarose gel and the 4200 bp EcoRI-HindIII fragment containing the origin of replication of B. subtilis and the CAT gene were eluted and purified by the "Gene clean" system (Vogelstein B., Gillespie D. (1979) P.N.A.S. 76:615).

Simultaneously, plasmid pSM289 (5 μg) was digested in 20 μl of buffer mixture with 10 U HindIII at 37° C. for 1 hour and, after checking the resulting cut by electrophoresis on agarose gel, with 5 U of EcoRI at 37° C. for 15 minutes.

The fragment of DNA EcoRI-HindIII (approx. 2400 bp) was then isolated from the digestion mixture by electrophoresis on agarose gel and subsequent electro-elution.

B) Construction of pSM290

500 ng of the 4200 bp fragment and 1 μg of the 2400 bp fragment were then ligated in 15 μl of ligation buffer in the presence of 1 U of T4 DNA ligase at 15° C. overnight. 300 ng of the aforementioned mixture were used to transform 100 μl of competent B. subtilis SMS108 cells and the transformants were selected on VY medium mixed with chloramphenicol.

The plasmid DNA was extracted from the resulting clones and subsequently subjected to analysis by restriction.

Two out of the plasmids analyzed were found to possess the EcoRI-HindIII fragment containing the isoamylase gene in the expected structure.

One of these plasmids, called pSM290, is characterised by the restriction map in FIG. 12.

The nucleotide sequence for checking the correct assembling of plasmid pSM290 was obtained by using the Boehringer "puc sequencing kit".

Example 6

Expression and secretion of isoamylase

A) Assay of isoamylase activity on a plate

The method described by Harada (Sugimoto T., et al. (1974) Appl. Microbiol., 28:336) for demonstrating isoamylase activity was modified in order to pick out clones capable of producing isoamylase, among the various recombinant colonies.

Cells of E. coli DH1 containing plasmid pSM289 were grown in minimum medium M9+0.2% glucose and/or maltose (6 g/l $Na_2$ $HPO_4$, 3 g/l $KH_2PO_4$, 0.5 g/l NaCl, 1 g/l $NH_4Cl$, 2 mM $MgSO_4$, 0.1 mM $CaCl_2$, 1.5% agar), plus 1% amylopectin as substrate and inductor and 50 μg/ml ampicillin. The pH of the medium was brought to 6.8 with HCl.

The cells of B. subtilis SMS108 transformed by plasmid pSM290 were grown on M9 medium +0.2% glucose and/or maltose mixed with 1% amylopectin, 5 μg/ml chloramphenicol and 50 μg/ml nisidine and leucine.

Another medium used for B. subtilis was MB containing 0.2% glucose and/or maltose (2 g/l $(NH_4)_2$ $SO_4$, 18.3 g/l $K_2HPO_4$ $3H_2O$, 6 g/l $KH_2PO_4$, 1 g/l Na-citrato. 2H 0, 0.2 g/l $MgSO_4$ $7H_2O$) plus 1% amylopectin, 1.5% agar, 5 μg/ml chloramphenicol and 50 μg/ml of the aforementioned aminoacids.

The pH of both media was adjusted to 6.0.

The colonies were grown at 37° C. for about 24 hours and then exposed to iodine vapours (2 g iodine in flakes, 1 g KI, 25 ml ethanol 95, 25 ml water).

After 2 minutes' exposure, the clones of E. coli DH2 (pSM289) producing isoamylase showed a marked blue ring, whereas clones of B. subtilis SMS108 (pSM290) showed a lighter ring due to interference with alpha amylase produced by the last-mentioned strain.

B) Assay of isoamylase activity in liquid

Cells of E. coli DH2 (pSM289) and B. subtilis SMS108 (pSM290) were inoculated in 50 ml of M9 medium and M9 and MB and cultivated with gentle agitation at 37° C. for 16 hours.

Next, the periplasm fraction was extracted from the E. coli cells and the total proteins from E. coli and B. subtilis.

In practice, the periplasm proteins were extracted by the method of Koshland and Botstein (1980) Cell, 20 (3), 749:780, operating as follows. 2 ml of bacterial culture were centrifuged in an Eppendorf centrifuge at 12000 rpm for 30 seconds.

The pellet was then recovered, washed twice with 30 mM acetate buffer (pH 4) and 50 mM NaCl, centrifuged as stated hereinbefore and finally resuspended in 1 ml of 20% saccharose, 30 mM acetate buffer at pH4 and 1 mM EDTA.

The resulting suspension was kept at ambient temperature (20°–25° C.) for 5 minutes, agitated at intervals, centrifuged for 5 minutes at 4° C., and finally resuspended in 1 ml of distilled water kept at 4° C.

The resulting suspension was incubated in an ice bath for 10 minutes and then centrifuged at 4° C. and at 3000 rpm for 10 minutes, the desired periplasm fraction being obtained in the supernatant.

All the solutions used contained protease inhibitors, i.e. PMSF (phenyl-methyl-sulphonyl chloride) and EDTA in final concentrations of 1 mM and 5 mM respectively.

400 μl of this fraction, concentrated if required by the AMYCON system, were used for assaying isoamylase activity.

The total proteins were extracted by centrifuging 10 ml of each bacterial culture at 5000 rpm for 5 minutes at 4° C.

The resulting cell pellets were washed twice with one volume of 10 mM acetate buffer at pH 4, 50 mM NaCl 1 mM PMSF and 5 mM EDTA and recentrifuged as stated hereinbefore.

The pellets were then resuspended in 5 ml of 10 mM acetate buffer at pH 4 in the presence of 1 mM PMSF.

The cell suspensions were then subjected to French-press (AMINCO) treatment at 2500 psi in order to break the bacterium wall and expel the cell components.

In the case of B. subtilis cells, lysis treatment by French-Press was preceded by incubation with 5 mg/ml lysozyme at 37° C. for 10 minutes in order to reduce the resistance of the cell wall.

The isoamylase activity was then determined in the supernatant, in the cell extract and in the periplasm extract by the method described by Yokobayashi A. et al. (1970) B.B.A., 212:458–469).

In practice, 2 ml of a 1% solution (w/v) of amylopectin (Sigma) in water kept at 40° C. were mixed with 400 µl of mM acetate buffer pH 4 and 400 µl of the solution for assay.

The resulting mixture was then kept at 40° C. for 1 hour, a sample (400 µl) for analysis being taken at the beginning ($t_0$) and the end ($t_1$) of the reaction.

Before development of the colorimetric reaction and the spectrophotometer reading, the samples were centrifuged for 30 seconds at 10000 rpm in an Eppendorf centrifuge at ambient temperature in order to remove suspended material which could interfere with the determination of absorbency.

After centrifuging, the samples were mixed with 400 µl of iodine reagent (0.2% I (w/v), 2% KI (w/v) and 0.2% H SO (w/v) brought to 20 ml with water and kept at ambient temperature for about 15 minutes.

The reading was made in a Perkin-Elmer mod 551 S spectrophotometer at 610 nm, against a blank prepared as described hereinbefore, the sample being replaced by acetate buffer, A positive control was also prepared, using purified isoamylase.

The term "isoamylase unit" means the quantity of isoamylase capable of increasing the spectrophotometer reading at 610 nm by 0.01 OD in 1 hour at 40° C.

The results for *E. coli* and *B. subtilis* are given in Tables 1 and 2 respectively.

TABLE 1

|  | Units/ml |
| --- | --- |
| Blank | 0 |
| Isoamylase (50 ng) (positive control) | 78 |
| *E. coli* (pSM 289) medium | 4.2 |
| *E. coli* (pSM 289) cell extract | 13.5 |
| *E. coli* (pSM 289) periplasm | 8.2 |

TABLE 2

|  | Units/ml |
| --- | --- |
| Blank | 0 |
| Isoamylase (20 ng) | 8.9 |
| *B. subtils* (pSM 268) medium | 0 |
| *B. subtils* (pSM 268) cell extract | 0 |
| *B. subtils* (pSM 290) medium | 89.4 |
| *B. subtils* (pSM 290) cell extract | 7.8 |

TABLE 2-continued

|  | Units/ml |
| --- | --- |
| Pseudomonas SMPI medium | 102.3 |

As shown by the data in Table 2, *B. subtilis* when transformed by plasmid pSM290 is capable not only of synthesizing isoamylase in quantities comparable with those from the original strain of Pseudomonas SMPI but, more particularly, of secreting the enzyme in the culture medium. Furthermore, *B. subtilis* (pSM290) takes only 16 hours to reach the optimum production level of the aforementioned enzyme, as compared with 5 days for Pseudomonas SMPI.

*Bacillus subtilis* containing the plasmid pSM290 was deposited pursuant to, and in satisfaction of, the requirements of the Budapest Treaty on the International Recognition of the Deposit of Microorganisms for the Purposes of Patent Procedures with the American Type Culture Collection (ATCC), 12301 Parklawn Drive, Rockville, Md. 20852 under the ATCC Accession No. 69127.

We claim:

1. A *Bacillus subtilis* host micro-organism transformed with a replicable recombinant DNA molecule, for expression and secretion of isoamylase, obtained by ligating a cloning vector with the structural gene of isoamylase, isolated from Pseudomonas SMP1 comprising the nucleotide sequence having the formula:

(5') ATG AAG TGC CCA AAG ATT CTC GCC GCG CTG CTT GGC
TGC GCG GTG CTC GCT GGT GTG CCC GCA ATG CCG GCG CAT GCG (3')

at its terminal 5'where the sequence codes for the secretion signal peptide of isoamylase.

2. A method for preparing isoamylase, said method comprising:

(a) transforming a *Bacillus subtilis* host micro-organism with a replicable recombinant DNA molecule as defined in claim 1, (b) culturing the resulting transformed micro-organism in a liquid environment in the presence of sources of carbon, nitrogen and mineral salts at pH 6 and at a temperature of 30° to 40° C., and (c) recovering the isoamylase produced by the cultured micro-organism.

3. The plasmid pSM290.

* * * * *